United States Patent
Motheram et al.

(10) Patent No.: US 11,737,989 B2
(45) Date of Patent: Aug. 29, 2023

(54) CLEVIDIPINE NANOPARTICLES AND PHARMACEUTICAL COMPOSITIONS THEREOF

(71) Applicant: CHIESI Farmaceutici S.p.A., Parma (IT)

(72) Inventors: Rajeshwar Motheram, Dayton, NJ (US); David C. Hanley, Sr., Brookfield, CT (US); Akif Emre Tureli, Saarlouis (DE); Monika Kanter, Saarburg (DE)

(73) Assignee: CHIESI FARMACEUTICI S.P.A., Parma (IT)

( * ) Notice: Subject to any disclaimer, the term of this patent is extended or adjusted under 35 U.S.C. 154(b) by 0 days.

(21) Appl. No.: 15/312,461

(22) PCT Filed: May 19, 2015

(86) PCT No.: PCT/US2015/031470
§ 371 (c)(1),
(2) Date: Nov. 18, 2016

(87) PCT Pub. No.: WO2015/179334
PCT Pub. Date: Nov. 26, 2015

(65) Prior Publication Data
US 2017/0087093 A1    Mar. 30, 2017

Related U.S. Application Data

(60) Provisional application No. 62/000,119, filed on May 19, 2014.

(51) Int. Cl.
*A61K 9/51* (2006.01)
*A61K 9/00* (2006.01)
(Continued)

(52) U.S. Cl.
CPC .......... *A61K 9/5123* (2013.01); *A61K 9/0019* (2013.01); *A61K 31/4422* (2013.01); *A61K 47/10* (2013.01)

(58) Field of Classification Search
None
See application file for complete search history.

(56) References Cited

U.S. PATENT DOCUMENTS 5,453,523 A * 9/1995 Weete ..................... C07F 9/103
554/10
5,739,152 A    4/1998 Andersson
(Continued)

FOREIGN PATENT DOCUMENTS

CN    103479577    9/2013
CN    103479577 *  1/2014
(Continued)

OTHER PUBLICATIONS

English language translation of CN 103479577 (Year: 2014).*
(Continued)

*Primary Examiner* — Dominic Lazaro
(74) *Attorney, Agent, or Firm* — Vorys, Sater, Seymour and Pease; Maryellen Feehery Hank

(57) ABSTRACT

Provided is a pharmaceutical composition comprising clevidipine in a sterile, ready to use, physically stable, aqueous
(Continued)

dispersion of nanoparticles that stabilizes clevidipine against formation of impurities and is suitable for parenteral administration.

24 Claims, 6 Drawing Sheets

(51) Int. Cl.
*A61K 31/4422* (2006.01)
*A61K 47/10* (2017.01)

(56) References Cited

U.S. PATENT DOCUMENTS

| | | | |
|---|---|---|---|
| 5,856,346 A | 1/1999 | Andersson | |
| 6,350,877 B1 | 2/2002 | Mattson et al. | |
| 8,697,131 B2 | 4/2014 | Tuereli | |
| 2010/0152077 A1* | 6/2010 | Allston | B01D 61/425 508/165 |
| 2011/0229559 A1* | 9/2011 | Prestidge | A61K 9/5115 424/450 |
| 2012/0088804 A1* | 4/2012 | Motheram | A61K 31/4418 514/356 |
| 2012/0322835 A1 | 12/2012 | Motheram et al. | |
| 2013/0012551 A1* | 1/2013 | Baumstuemmler | B01J 2/04 514/356 |
| 2013/0158079 A1 | 6/2013 | Motheram et al. | |
| 2013/0243886 A1 | 9/2013 | Hu et al. | |
| 2014/0121247 A1 | 5/2014 | Spindler, Jr. et al. | |
| 2014/0127311 A1 | 5/2014 | Beck-Broichsitter | |
| 2016/0067186 A1 | 3/2016 | Shah et al. | |

FOREIGN PATENT DOCUMENTS

| | | |
|---|---|---|
| CN | 103479577 A | 1/2014 |
| WO | 2013030725 | 8/2012 |
| WO | 2014052634 A1 | 4/2014 |

OTHER PUBLICATIONS

Frisken, B. Revisiting the method of cumulants for the analysis of dynamic light-scattering data. Applied Optics vol. 40, Issue 24, pp. 4087-4091 (2001).

Translation of Official Action—Notification of the Results of the Patentability Assessment of Invention; Application 2016149538/04(079547); pp. 1-9.

Gyllenhaal, O; Fast enantioselective separation of clevidipine and a dihydropyridine substituted acid by SFC on Chiralpak AD; Fresenius Journal of Analytical Chemistry (2001) 369:54-56.

Vertelov, G. K.; The use of nanoparticles in the electrochemical analysis of biological objects; Journal of analytical chemistry; 2007: v. 62; 9; pp. 903-915.

Abaeva, L.F. et al.; Nanoparticles and Nanotechnologies Today and Beyond; M.F. Vladimirsky Moscow Regional Clinical and Research Institute (MONIKI); No. 22'2010; pp. 10-16.

Krosnyuk, I.I. et al.: "Pharmaceutical technology: Technology of dosage forms: textbook for students of higher educational institutions"— Publishing House Academiya, end ed., sr.—2006, pp. 297-299.

* cited by examiner

CLEVIDIPINE NANOPARTICLES AND PHARMACEUTICAL COMPOSITIONS THEREOF

CROSS REFERENCE TO RELATED APPLICATIONS

This application is a continuation of International Application No. PCT/US2015/031470, filed on May 19, 2015, which claims priority from U.S. Provisional Patent Application No. 62/000,119 filed on May 19, 2014, the contents of both applications are hereby expressly incorporated by reference herein.

FIELD OF THE INVENTION

The instant invention relates to pharmaceutical formulations comprising clevidipine in a sterile, ready to use, aqueous dispersion of nanoparticles that are stable against formation of impurities and suitable for parenteral administration.

All documents cited to or relied upon below are expressly incorporated herein by reference.

BACKGROUND OF THE INVENTION

Clevidipine is a dihydropyridine calcium channel blocker that reduces blood pressure in a subject to which it is administered. It is characterized as a short-acting, highly selective drug that is rapidly metabolized and exhibiting an initial phase half-life of about one minute. Therefore, clevidipine is used in a hospital setting as an intravenous injection. Clevidipine is further characterized by having negligible solubility in water and moderate solubility in lipids. In addition, clevidipine is chemically unstable when in contact with water. Therefore clevidipine was developed as an oil-in-water emulsion (Cleviprex®). While the Cleviprex emulsion formulation addresses the physicochemical challenges of clevidipine and provides a ready to use product, significant limitations remain.

The emulsion formulation contains disodium edetate (EDTA) as a microbial growth retardant. However, even with strict aseptic technique during handling, the product needs to be discarded within 12 hours of opening, as prolonged use could still potentially support microbial growth in the event of inadvertent extrinsic contamination. Furthermore, the daily dose of Cleviprex® is limited due to its high lipid content, and its use is restricted in patients with hyperlipidemia and other related lipid disorders. Additionally, Cleviprex® requires refrigeration for long term storage, which is costly and could potentially restrict its use in emergency and ambulatory care situations.

Accordingly, there exists a need for an aqueous clevidipine formulation that has long term stability under ambient storage conditions and which does not support microbial growth and does not contribute to lipid load while still preserving the unique pharmacokinetics (fast onset of action and offset) of clevidipine. Designing such a formulation for parenteral administration is challenging considering clevidipine's negligible water solubility, the need for its stability sake to shield it from aqueous contact and the need to maintain its unique pharmacokinetic/pharmacodynamic performance. Such a formulation would provide greater ease of handling and result in cost savings to health care providers and patients by decreasing clevidipine waste and reducing the time-consuming efforts involved with cold-chain shipment and storage and with replacement of unemptied vials due to microbial growth considerations. Additionally, such a formulation would enable easier access to patients requiring ambulatory care.

The conventional nanoparticle formulations such as solid lipid nanoparticles, albumin stabilized nanoparticles or liposomes could potentially increase the stability of clevidipine in water at ambient temperatures. However, due to the specific characteristics of these particles, such formulations are not suitable for immediate release applications where the onset of action is expected immediately after parenteral administration of the drug. The nanoparticle formulations, listed above, have a long residency time in blood and control release of the active ingredient over time, which would impact the pharmacokinetics of clevidipine if utilized for its formulation.

SUMMARY OF THE INVENTION

The present invention is directed to a therapeutic nanoparticle, comprising clevidipine, or a pharmaceutically acceptable salt thereof, and at least one excipient. In one embodiment, clevidipine comprises the core of the nanoparticle and the at least one excipient comprises an outer portion substantially surrounding the core.

The invention is further directed to a therapeutic nanoparticle, comprising clevidipine, or a pharmaceutically acceptable salt thereof, and at least one excipient made by colliding clevidipine, or a pharmaceutically acceptable salt thereof, and said at least one excipient in a microjet reactor.

The invention is also directed to a pharmaceutical composition, comprising a therapeutically effective amount of a therapeutic nanoparticle comprising clevidipine, or a pharmaceutically acceptable salt thereof, and at least one excipient and a pharmaceutically acceptable carrier.

The invention is additionally directed to a method of treating hypertension, comprising the step of administering a therapeutically effective amount of a therapeutic nanoparticle, said nanoparticle comprising clevidipine, or a pharmaceutically acceptable salt thereof, and at least one excipient, to a patient in need thereof.

DETAILED DESCRIPTION OF THE INVENTION

Figure 1:
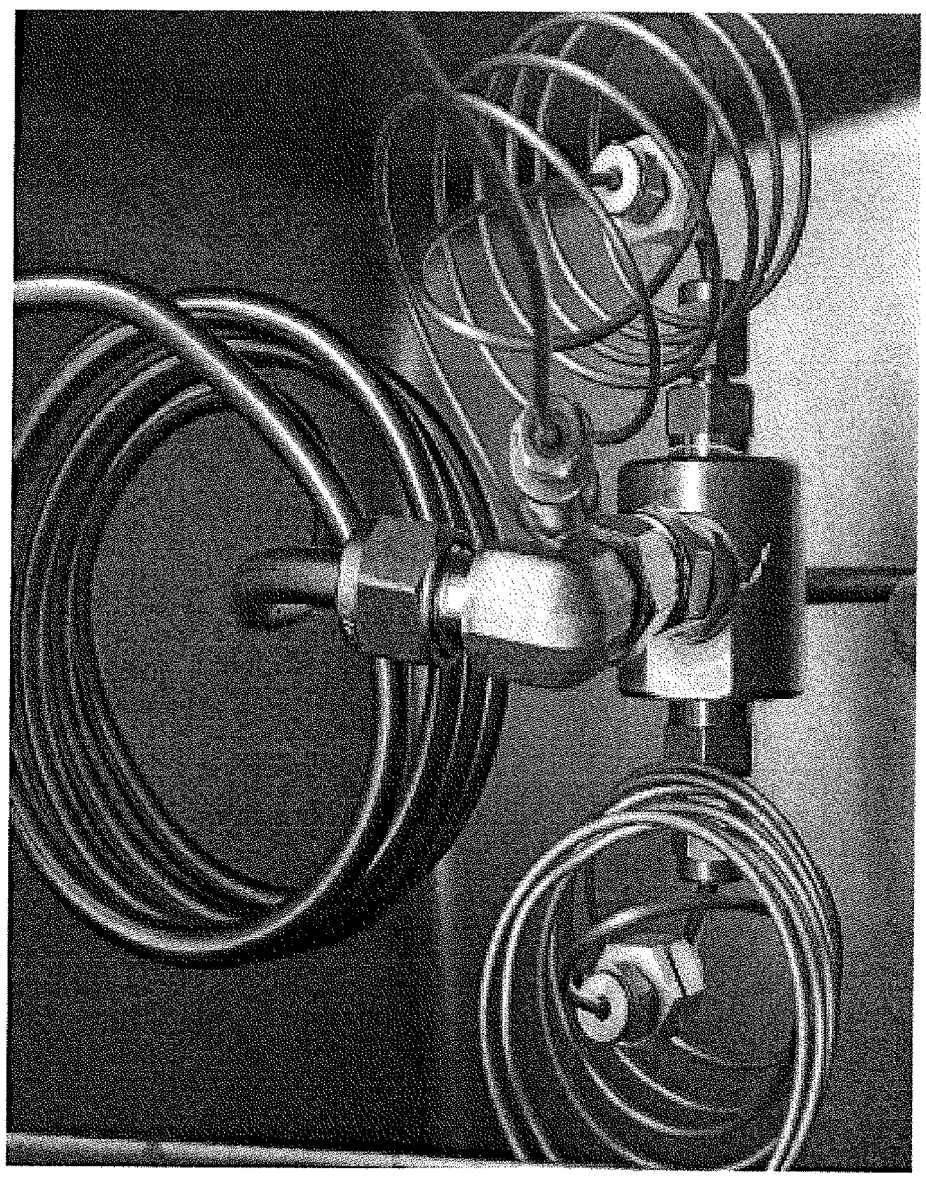
FIG. 1 is a photograph showing a microjet reactor assembly useful for forming the nanoparticles of the invention.

It is to be understood that the figures and descriptions of the present invention have been simplified to illustrate elements that are relevant for a clear understanding of the present invention, while eliminating, for the purpose of clarity, many other elements found in typical pharmaceutical compositions and methods of stabilization. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

The present invention generally relates to nanoparticles that include an active or therapeutic agent or drug, and methods of making and using such therapeutic nanoparticles. The inventors discovered that it is possible to prepare stable and ready to use clevidipine nanoparticle colloidal dispersions with particle size and homogeneity of the particles appropriate for parenteral application. Stable nanoparticle formulations of clevidipine were designed such that they can be stored at ambient temperatures with the desired immediate release characteristics for parenteral application. This was accomplished, for example, using three different approaches for the electrostatic and stearic stabilization of the nanoparticles. In these three approaches different excipient combinations were used where the first approach incorporated a combination of water insoluble excipients, the second approach a combination of water soluble and water insoluble excipients and the third approach a combination of water soluble excipients.

In these approaches, it was expected that the water insoluble excipients could stabilize clevidipine entrapped in the nanoparticles while the water soluble excipients could facilitate faster release of clevidipine from the nanoparticles. Thus, it was anticipated that a combination of water soluble and water insoluble excipients might provide the desired clevidipine stability and immediate release, with the immediate release component of the target product profile being the operative challenge. It was surprisingly found, however, that all of the three approaches showed the desired stability at ambient conditions, and immediate release in blood was observed for the formulations containing water insoluble excipients where most complete shielding from water but slow release were expected.

Thus, in one embodiment of the invention, provided is a therapeutic nanoparticle, comprising clevidipine, or a pharmaceutically acceptable salt thereof, and at least one excipient.

In another embodiment of the invention, provided is a therapeutic nanoparticle, wherein said clevidipine comprises a core portion of said nanoparticle and said at least one excipient comprises an outer portion substantially surrounding said core.

In another embodiment of the invention, provided is a therapeutic nanoparticle, wherein said clevidipine substantially comprises the core of said nanoparticle and said at least one excipient substantially comprises the outer portion of said nanoparticle.

In another embodiment of the invention, provided is a therapeutic nanoparticle, wherein said at least one excipient is water soluble or water insoluble or more than one excipients are present in combinations thereof.

In another embodiment of the invention, provided is a therapeutic nanoparticle, wherein said water soluble excipient is vitamin E TPGS, polysorbate 80, polysorbate 20, Triton X-100, lauryl glucoside, NP-40, oleyl alcohol, sorbitans (monosterate tristearate), stearyl alcohol, nonoxynols, Cremophore (RH 60 or EL), Solutol HS 15, plutonic acid, sodium dodecyl sulfate (SDS), bile acid salts, polyethylene glycol or polypropylene glycol, or combinations thereof.

In another embodiment of the invention, provided is a therapeutic nanoparticle, wherein said water insoluble excipient is vitamin E, and its derivatives, bile acid and its derivatives and phospholipid derivatives, lecithin, lysolecithin, phosphotidylserine, glycerophosphocholine, oleic acid, glycerol, inositol, diethylenetriaminepentaaceticacid, polyoxyethylene castor, polyoxyethylenehydrogenated castor oil base or polyoxyethylene sorbitan monolaurate, or combinations thereof.

In another embodiment of the invention, provided is a therapeutic nanoparticle, comprising at least one water soluble excipient and at least one water insoluble excipient.

In another embodiment of the invention, provided is a therapeutic nanoparticle, wherein said nanoparticle is less than 900 nm in size.

In another embodiment of the invention, provided is a therapeutic nanoparticle, wherein said nanoparticle is less than 800 nm in size.

In another embodiment of the invention, provided is a therapeutic nanoparticle, wherein said nanoparticle is less than 700 nm in size.

In another embodiment of the invention, provided is a therapeutic nanoparticle, wherein said nanoparticle is less than 600 nm in size.

In another embodiment of the invention, provided is a therapeutic nanoparticle, wherein said nanoparticle is less than 500 nm in size.

In another embodiment of the invention, provided is a therapeutic nanoparticle, wherein said nanoparticle is less than 400 nm in size.

In another embodiment of the invention, provided is a therapeutic nanoparticle, wherein said nanoparticle is less than 300 nm in size.

In another embodiment of the invention, provided is a therapeutic nanoparticle, wherein said nanoparticle is less than 200 nm in size.

In another embodiment of the invention, provided is a therapeutic nanoparticle, wherein said nanoparticle is less than 100 nm in size.

In another embodiment of the invention, provided is a therapeutic nanoparticle, wherein said nanoparticle is less than 50 nm in size.

In another embodiment of the invention, provided is a therapeutic nanoparticle, wherein said nanoparticle is from 50 nm to 400 nm in size.

In another embodiment of the invention, provided is a therapeutic nanoparticle, wherein said nanoparticle is from 100 nm to 600 nm in size.

In another embodiment of the invention, provided is a therapeutic nanoparticle, wherein said nanoparticle is from 100 nm to 250 nm in size.

In another embodiment of the invention, provided is a therapeutic nanoparticle, wherein said nanoparticle is from 200 nm to 450 nm in size.

In another embodiment of the invention, provided is a therapeutic nanoparticle, comprising clevidipine, or a pharmaceutically acceptable salt thereof, and at least one excipient made by colliding clevidipine, or a pharmaceutically acceptable salt thereof, and said at least one excipient in a microjet reactor.

In another embodiment of the invention, provided is a pharmaceutical composition, comprising a therapeutically effective amount of a therapeutic nanoparticle, comprising clevidipine, or a pharmaceutically acceptable salt thereof, and at least one excipient, and a pharmaceutically acceptable carrier.

In another embodiment of the invention, provided is a pharmaceutical composition, wherein said therapeutic nanoparticle is in an aqueous colloidal suspension.

In another embodiment of the invention, provided is a method of treating hypertension, comprising the step of administering a therapeutically effective amount of therapeutic nanoparticle, comprising clevidipine, or a pharmaceutically acceptable salt thereof, and at least one excipient to a patient in need thereof.

In another embodiment of the invention, provided is a method, wherein said therapeutic nanoparticle is administered parenterally.

In another embodiment of the invention, provided is a method, wherein said therapeutic nanoparticle is administered intravenously.

As used herein, the term "clevidipine" shall mean and include all varieties or forms of clevidipine. Unless otherwise specified, examples of such forms include all pharmaceutically acceptable salts, esters, isomers, stereo isomers, crystalline and amorphous forms. The amount of clevidipine in the formulations of the present invention can vary depending on the total overall volume of the formulation and the concentration of the other components.

As used herein, the term "therapeutic nanoparticle" shall mean a nanoparticle comprising a therapeutic agent or active pharmaceutical ingredient. The therapeutic nanoparticle provides a therapeutic effect when administered to a patient in need thereof.

As used herein, the term "pharmaceutically acceptable salt" shall refer to salts prepared from pharmaceutically acceptable non-toxic bases or acids including inorganic or organic bases and inorganic or organic acids. Examples of salts derived from inorganic bases include aluminum, ammonium, calcium, copper, ferric, ferrous, lithium, magnesium, manganic, manganous, potassium, sodium, zinc, and the like. In certain embodiments are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

As used herein, the term "pharmaceutically acceptable ester" shall refer to esters prepared by reaction of an oxoacid with a compound containing a hydroxyl group. Generally esters are derived from an inorganic or organic acid and an alcohol. More commonly esters are prepared by condensing an organic acid and an alcohol. Examples of suitable esters that may be used in the formulations of the present invention include butyric acid esters, such as those prepared in accordance with teachings in U.S. Pat. Nos. 5,856,346, 5,739,152, 6,350,877 and the like.

Nanoparticles

The nanoparticles of the invention are small particles comprising clevidipine, or a pharmaceutically acceptable salt thereof, and at least one excipient. In general, the term "nanoparticle" refers to any particle having an average size of less than 1000 nm. By "average size" is meant the mean effective diameter as measured by dynamic light scattering methodology, using for example, Brookhaven Instruments' 90Plus or Malvern Zetasizer Z90 particle sizing instrument.

The average size of the nanoparticles can be, for example, less than 900 nm, less than 800 nm, less than 700 nm, less than 600 nm, less than 500 nm, less than 400 nm, less than 300 nm, less than 200 nm, less than 100 nm and less than 50 nm. The width of the particle size distribution in suspension is given by the "polydispersity" or "PDI" of the particles, which is defined as the relative variance in the correlation decay rate distribution, as is known by one skilled in the art. See B. J. Fisken, "Revisiting the method of cumulants for the analysis of dynamic light-scattering data," Applied Optics, 40(24), 4087-4091 (2001) for a discussion of cumulant diameter and polydispersity. In another embodiment, the polydispersity of a given formulation of nanoparticles is less than 0.6. In another embodiment, the polydispersity of a given nanoparticle formulation can be less than 0.5, less than 0.4, less than 0.3, less than 0.2 and less than 0.1.

The nanoparticles can exist in a number of different configurations. In one embodiment, the nanoparticles comprise a core, the core comprising clevidipine or a pharmaceutically acceptable salt thereof. As used herein, the term "core" refers to the interior portion of the nanoparticle. The nanoparticles also have a "surface" or an "outer" portion. The nanoparticles can, thus, have a core (i.e., the interior portion) and a surface or outer portion substantially surrounding the core. In one embodiment of the invention, the core is substantially comprised of clevidipine and the outer portion is substantially comprised of one or more excipients.

In another embodiment, the concentration of clevidipine can vary throughout the nanoparticle with the concentration of clevidipine being highest, for example, at the core. For example, the nanoparticles of the invention can comprise a matrix of excipients and clevidipine, such that an amount of clevidipine can be dispersed in the outer portion of the nanoparticle and an amount of the excipient or combination of excipients can be dispersed within the core of the nanoparticle, or combinations thereof. Thus, in some embodiments, clevidipine or a pharmaceutically acceptable salt thereof can be associated with at least part of the excipient outer portion. Some amount of clevidipine can, therefore, be associated with the surface of, encapsulated within, surrounded by, and/or dispersed or diffused throughout the excipient outer portion of the therapeutic nanoparticle.

In some embodiments, described herein below, materials may be adsorbed to the surface portion of the nanoparticle. Materials adsorbed to the surface portion of the nanoparticle are considered part of the nanoparticle, but are distinguishable from the core of the nanoparticle. Methods to distinguish materials present in the core versus materials adsorbed to the surface portion of the nanoparticle include (1) thermal methods, such as differential scanning calorimetry (DSC); (2) spectroscopic methods, such as X-ray diffraction (XRD), X-ray photoelectron spectroscopy (XPS), transmission electron microscopy (TEM) with energy dispersive X-ray (EDX) analysis, fourier transform infra red (FTIR) analysis, and raman spectroscopy; (3) chromatographic techniques, such as high performance liquid chromatography (HPLC), and gel-permeation chromatography (GPC); and (4) other techniques known in the art.

Excipients

In some embodiments, the clevidipine nanoparticles are stabilized with one or more water soluble (e.g, hydrophilic)

excipients, one or more water insoluble (e.g., lipophilic) excipients or a combination of one or more water soluble and one or more water insoluble excipients.

Examples of water soluble excipients include, but are not limited to, vitamin E TPGS, polysorbate 80, polysorbate 20, Triton X-100, lauryl glucoside, NP-40, oleyl alcohol, sorbitans (monosterate tristearate), stearyl alcohol, nonoxynols, Cremophore (RH 60 or EL), Solutol HS 15, plutonic acid, sodium dodecyl sulfate (SDS), bile acid salts, polyethylene glycol and polypropylene glycol and their combinations. Bile acid salts were selected from a group of salts of cholic acid, chenodeoxycholic acid, deoxycholic acid and urodeoxycholic acid. The excipients that were used, either alone or in combination for stabilization of clevidipine particles, included but were not limited to PEG/bile acid salts, bile acid salts/vitamin E TPGS, PEG/vitamin E TPGS.

Examples of water insoluble excipients include, but are not limited to, vitamin E, and its derivatives, bile acid and its derivatives and phospholipid derivatives, lecithin, lysolecithin, phosphotidylserine, glycerophosphocholine, oleic acid, glycerol, inositol, diethylenetriaminepentaaceticacid, polyoxyethylene castor, polyoxyethylenehydrogenated castor oil base, polyoxyethylene sorbitan monolaurate and combinations thereof. Phospholipid derivatives were selected from a group of natural phospholipids such as the ones isolated from egg yolk for soya beans, synthetic phospholipids, phosphotadylcholine, and hydrogenated phospholipids. Bile acid derivatives were selected from a group of cholic acid, chenodeoxycholic acid, deoxycholic acid and urodeoxycholic acid. The excipients that were used, either alone or in combination for stabilization of clevidipine particles, included but were not limited to vitamin E derivatives/bile acid derivatives, vitamin E derivatives/phospholipid derivatives, bile acid derivatives /phospholipid derivatives.

In a certain embodiment, the clevidipine nanoparticles are stabilized by a combination of one or more water soluble excipients, selected from PEG 200, sodium deoxycholate and vitamin E TPGS, and one or more water insoluble excipients, selected from vitamin E, deoxycholic acid and phosphotidylcholine.

Any polymer can be used in accordance with the present invention. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers in accordance with the present invention are organic polymers.

The term "polymer" as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself.

Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments of the present invention include polydioxanone (PDO), polyhydroxyalkanoate, polyhydroxybutyrate, poly(glycerol sebacate), polyglycolide, polylactide, polycaprolactone, or copolymers or derivatives including these and/or other polymers.

In certain embodiments, contemplated biocompatible polymers may be biodegradable, i.e., the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

For instance, a contemplated polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other non-polymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers can be cationic polymers. In general, cationic polymers are able to condense and/or protect negatively charged strands of nucleic acids (e.g. DNA, RNA, or derivatives thereof). Amine-containing polymers such as poly(lysine), polyethylene imine (PEI), and poly(amidoamine) dendrimers are contemplated for use, in some embodiments, in a disclosed particle.

In some embodiments, polymers can be degradable polyesters bearing cationic side chains. Examples of these polyesters include poly(L-lactide-co-L-lysine), poly(serine ester), poly(4-hydroxy-L-proline ester).

Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R—O—R' bonds). In some embodiments of the invention, a biodegradable polymer, such as a hydrolyzable polymer, containing carboxylic acid groups, may be conjugated with poly(ethylene glycol) repeat units to form a poly(ester-ether). A polymer (e.g., copolymer, e.g., block copolymer) containing poly(ethylene glycol) repeat units can also be referred to as a "PEGylated" polymer.

It is contemplated that PEG may be terminated and include an end group, for example, when PEG is not conjugated to a ligand. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties.

Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like In one embodiment, the molecular weight of the polymers can be adjusted for effective treatment as disclosed herein. For example, the molecular weight of a polymer may influence particle degradation rate (such as when the molecular weight of a biodegradable polymer can be adjusted), solubility, water uptake, and drug release kinetics. For example, the molecular weight of the polymer can be adjusted such that the particle biodegrades in the subject being treated within a reasonable period of time (ranging from a few hours to 1-2 weeks, 3-4 weeks, 5-6 weeks, 7-8 weeks, etc.). A disclosed particle can for example comprise a diblock copolymer of PEG and PL(G)A, wherein for example, the PEG portion may have a number average molecular weight of about 1,000-20,000, e.g., about 2,000-20,000, e.g., about 2 to about 10,000, and the PL(G)A portion may have a number average molecular weight of about 5,000 to about 20,000, or about 5,000-100,000, e.g., about 20,000-70,000, e.g., about 15,000-50,000.

In certain embodiments, the polymers of the nanoparticles can be conjugated to a lipid. The polymer can be, for example, a lipid-terminated PEG. As described below, the lipid portion of the polymer can be used for self assembly with another polymer, facilitating the formation of a nanoparticle. For example, a hydrophilic polymer could be conjugated to a lipid that will self assemble with a hydrophobic polymer.

In another embodiment of the invention, the nanoparticles may be formulated with antioxidants. Examples of antioxidants may include, but are not limited to, acetylcysteine, ascorbyl palmitate, butylated hydroxyanisole ("BHA"), butylated hydroxytoluene ("BHT"), monothioglycerol, ascorbic acid, sodium ascorbate, sodium formaldehyde sulfoxylate, sodium metabisulfite, sodium bisulfate, propyl gallate, edetate ("EDTA") (e.g., disodium edetate), diethylenetriaminepentaacetic acid ("DTPA"), or any combinations thereof. Antioxidants may also comprise amino acids such as methionine, histidine, cysteine and those carrying a charged side chain, such as arginine, lysine, aspartic acid, and glutamic acid. Further, the antioxidant may be any stereoisomer (e.g., L-, D-, or a combination thereof) of any particular amino acid.

Preparation of Nanoparticles of the Invention

Clevidipine can be manufactured by reaction of 4-(2',3'-dichlorophenyl)-1,4-dihydro-5-methoxycarbonyl -2,6-dimethyl-3-pyridinecarboxylic acid with chloromethyl butyrate to obtain clevidipine. This reaction can be done optionally in the presence of a corresponding hydrogen carbonate, such as KHCO₃, in refluxing acetonitrile. Inorganic salts can be removed by filtration and the product is crystallized by the addition of isopropanol and water with subsequent cooling. It can also be crystallized by exchanging solvent from acetonitrile to a mixture of alcohol, such as ethanol or isopropanol, and water with repeated evaporations. In the further purification of the product the crystals are washed with a mixture of water and ethanol or isopropanol. The product can be dissolved in refluxing isopropanol, crystallized by cooling, isolated by filtration and finally washed with a water and isopropanol mixture. A more detailed description of the manufacturing process of clevidipine can be found in U.S. Pat. No. 6,350,877, the entire disclosure of which is incorporated by reference herein as if set forth in its entirety.

In embodiments of the invention, clevidipine may be present in an amount between about 0.01 mg/mL and about 100 mg/mL, or between about 0.05 mg/mL and about 50 mg/mL, or between about 0.1 mg/mL and about 25 mg/mL, or between about 1.0 mg/mL and about 10 mg/mL, or between about 2.5 mg/mL and 7.5 mg/mL, such as a concentration of 5.0 mg/mL. Moreover, if a specific concentration of clevidipine is desired the concentration can be adjusted, for example, by the addition of water.

In one embodiment of the invention, provided is a pharmaceutical composition comprising therapeutic nanoparticles of clevidipine, or a pharmaceutically acceptable salt thereof, wherein in said composition, the level of any single impurity is no more than 1.8% on a weight-to-weight basis when stored for at least three months at room temperature. In another embodiment of the invention, provided is a pharmaceutical composition comprising therapeutic nanoparticles of clevidipine, or a pharmaceutically acceptable salt thereof, wherein in said composition, the level of impurities is minimized to no more than 0.2% on a weight-to-weight basis for any of Substance 23, Substance 24, and Substance 25, and no more than 1.5% for H168/79 on a weight-to-weight basis when stored for at least three months at room temperature. The scheme below shows the clevidipine degradation pathways resulting in the impurities:

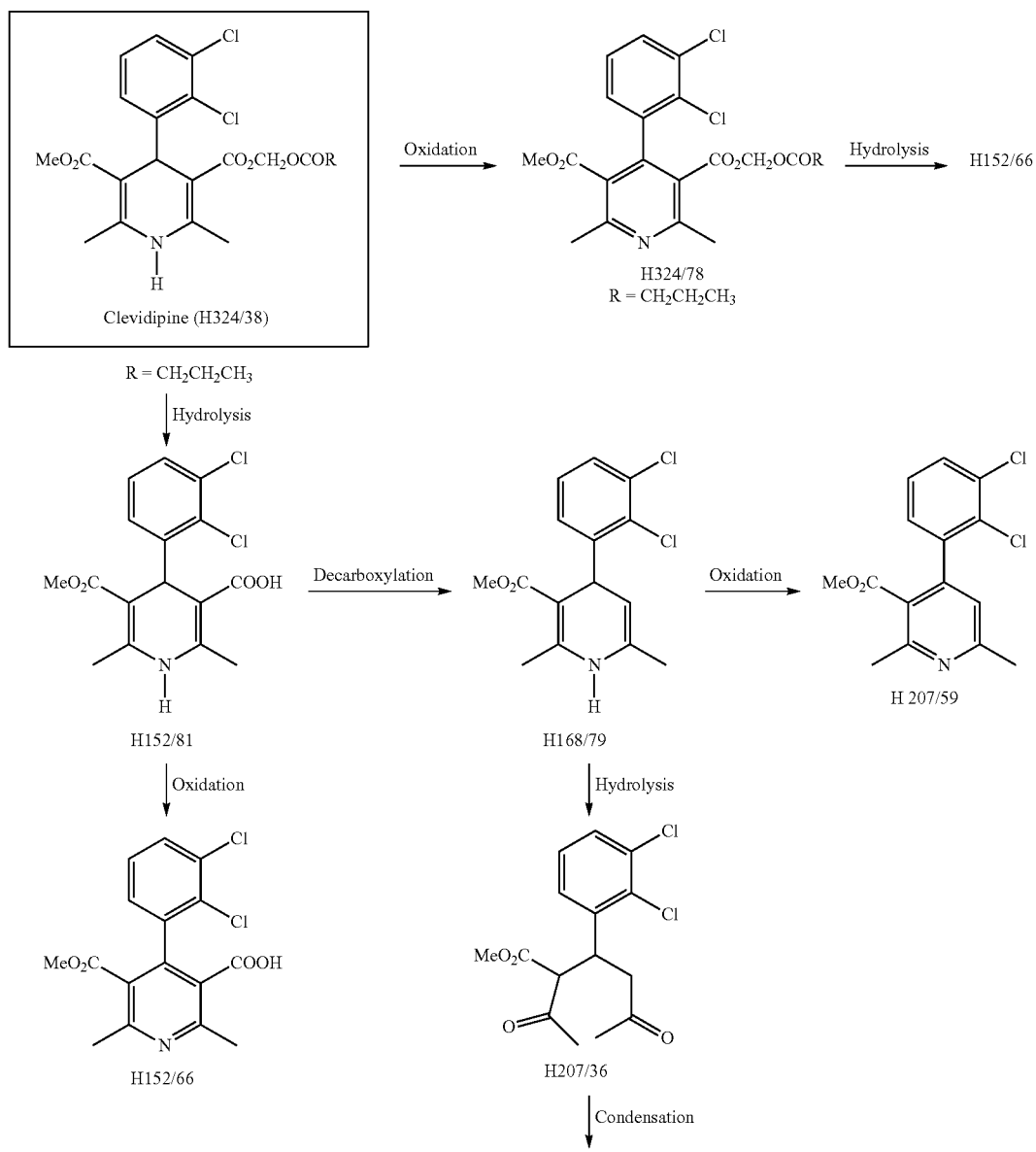

-continued

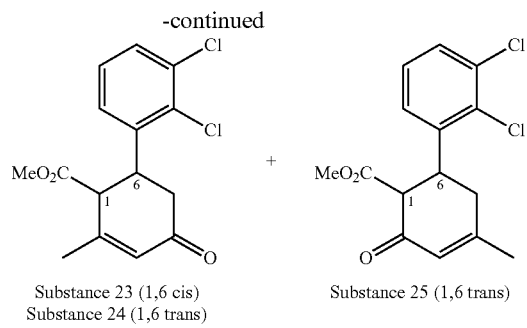

Substance 23 (1,6 cis)
Substance 24 (1,6 trans)

Substance 25 (1,6 trans)

Nanoparticles of the invention comprising clevidipine can be prepared using any device or method commonly used in the art. Such devices and methods can be found, for example, in U.S. Pat. No. 8,697,131 and US Published Application Serial No. 2013/0012551, the contents of both of which are expressly incorporated herein by reference in their entireties. FIGS. 1-5 show the method of making the inventive nanoparticles by using the microjet reactor device of MJR Pharmjet GmbH of Saarlouis, Germany.

In one embodiment, microjet reactors can be used to produce microparticles or nanoparticles of water-soluble and water-insoluble substances by controlled precipitation, co-precipitation and self-organization processes. In the reactor, a solvent, which contains at least one target molecule such as clevidipine, and a nonsolvent being mixed as jets that collide with each other in a microjet reactor at defined pressures and flow rates to effect very rapid precipitation, co-precipitation or a chemical reaction, during the course of which microparticles or nanoparticles are formed. The particle size is controlled by the temperature at which the solvent and nonsolvent collide, the flow rate of the solvent and the nonsolvent and/or the amount of gas, smaller particle sizes being obtained at lower temperatures, at high solvent and nonsolvent flow rates and/or in the complete absence of gas.

In one embodiment, the method of producing pharmaceutical drug particles of small particle size, such as the clevidipine nanoparticles, can comprise the following steps:
dissolving pharmaceutical drug particles, such as clevidipine, in a water-miscible solvent at high temperatures under pressure if needed;
pumping this drug solution through heated capillaries into the heated microjet reactor
collision of the liquid jet of drug solution with a liquid jet formed by another nozzle of the precipitation/spray-drying reactor, the latter jet consisting of water or an aqueous solution;
maintenance of a gaseous atmosphere at the collision point of the liquid jets by supplying gas to blow the precipitation zone free, or by at least partial vaporization of solvent and water in the collision zone as a result of the pressure drop following the passage of the jets through the respective nozzles, or, where a free jet reactor is used, by gravity-based removal of the dispersion mist;
extremely rapid mixing due to mixing taking place in the form of impinging jets in a gaseous atmosphere, with a mixing time of less than 100 ms, in another embodiment less than one ms; and
formation of nanoparticulate nuclei by very fast diffusion-controlled solvent/non-solvent precipitation at the collision point and the plate-like mixing zone of the liquid jets in a gaseous atmosphere.

Thus, in one embodiment for the preparation of nanoparticles, clevidipine is first dissolved in a water-miscible organic solvent such as ethanol, and a surface modifier is then dissolved in the solution. A pump is used to inject the solution via a pipe under raised pressure of up to more than one bar, in another embodiment up to more than 5 bar, in another embodiment up to more than 10 bar, through a nozzle into the precipitation reactor. The nozzle of the precipitation reactor serves simultaneously as a pressure regulating valve. The supply pipe, or infeed line, can be heated from the exterior, either by means of an electrical resistance heater or by a heating bath, said infeed line in another embodiment being of a spiral configuration (FIG. 1).

Figure 2:
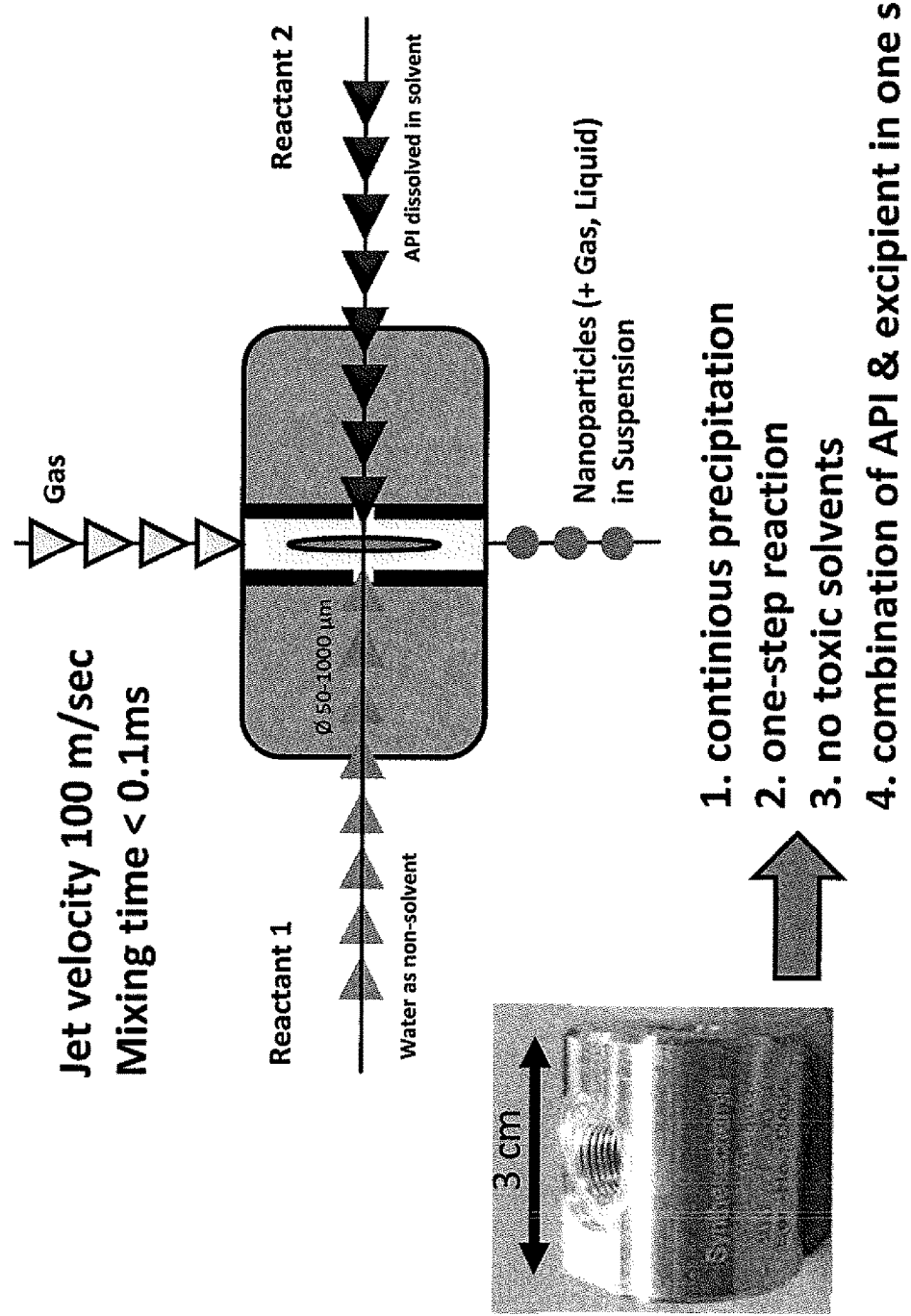
FIG. 2 is a schematic showing the process of how nanoparticles are formed in the interior of the microjet reactor (the inset being an external view of the reactor).
Figure 3:
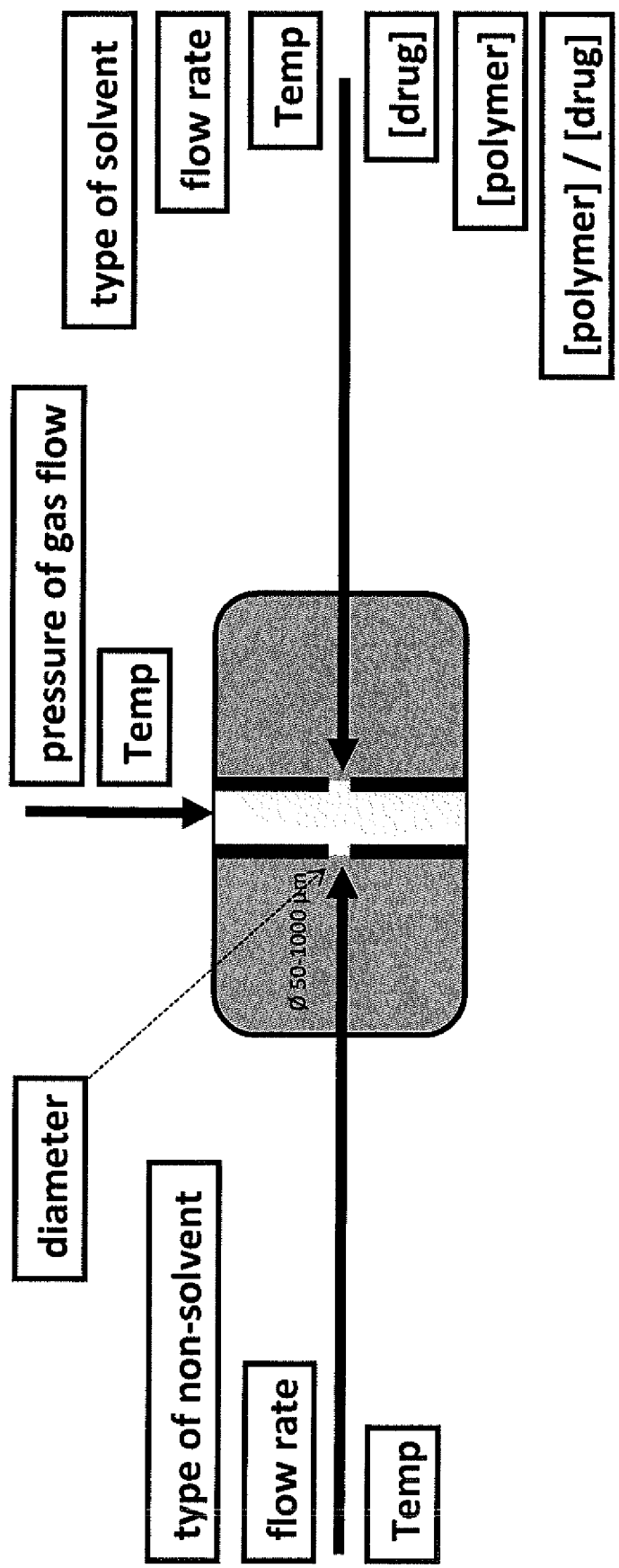
FIG. 3 is a schematic showing the process parameters used for the formation of the nanoparticles of the invention using the microjet reactor technology.

As seen in FIGS. 2 and 3, the reaction process makes use of controlled solvent/nonsolvent precipitation in such a way that solvent and non-solvent streams with flow rates exceeding 0.1 ml/min collide as impinging jets at a speed in another embodiment greater than 1 m/s, in another embodiment greater than 50 m/s. Solvent and nonsolvent are formed in nozzles to jets which are in another embodiment smaller than 1,000 µm, in another embodiment smaller than 500 µm and best of all smaller than 300 µm and have pressures generally of 1 bar, in another embodiment in excess of 5 bar and even in another embodiment in excess of 10 bar.

Figure 4:
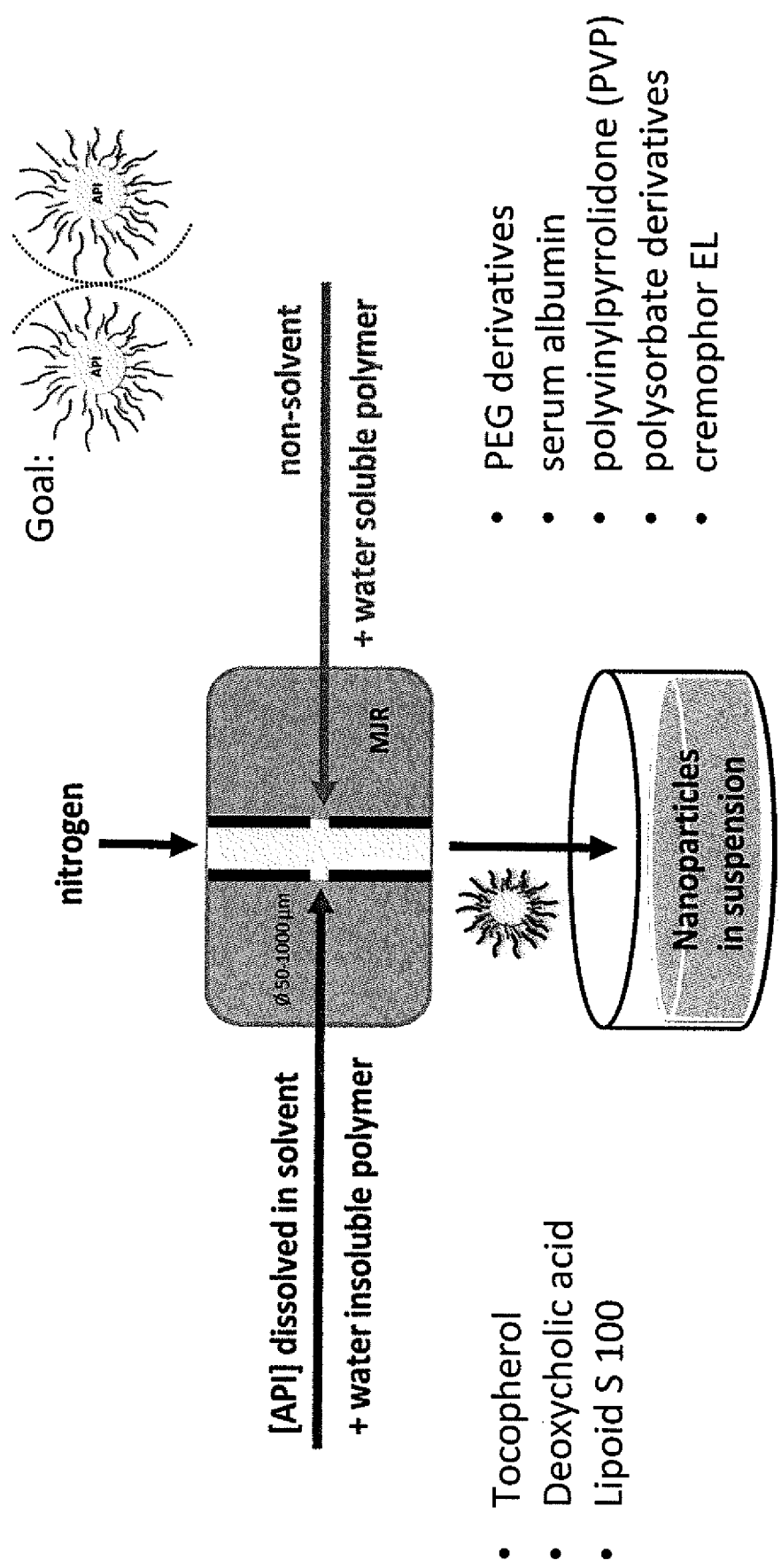
FIG. 4 is a schematic showing the precipitation of nanoparticles out of the reactor and in a colloidal suspension.
Figure 5:
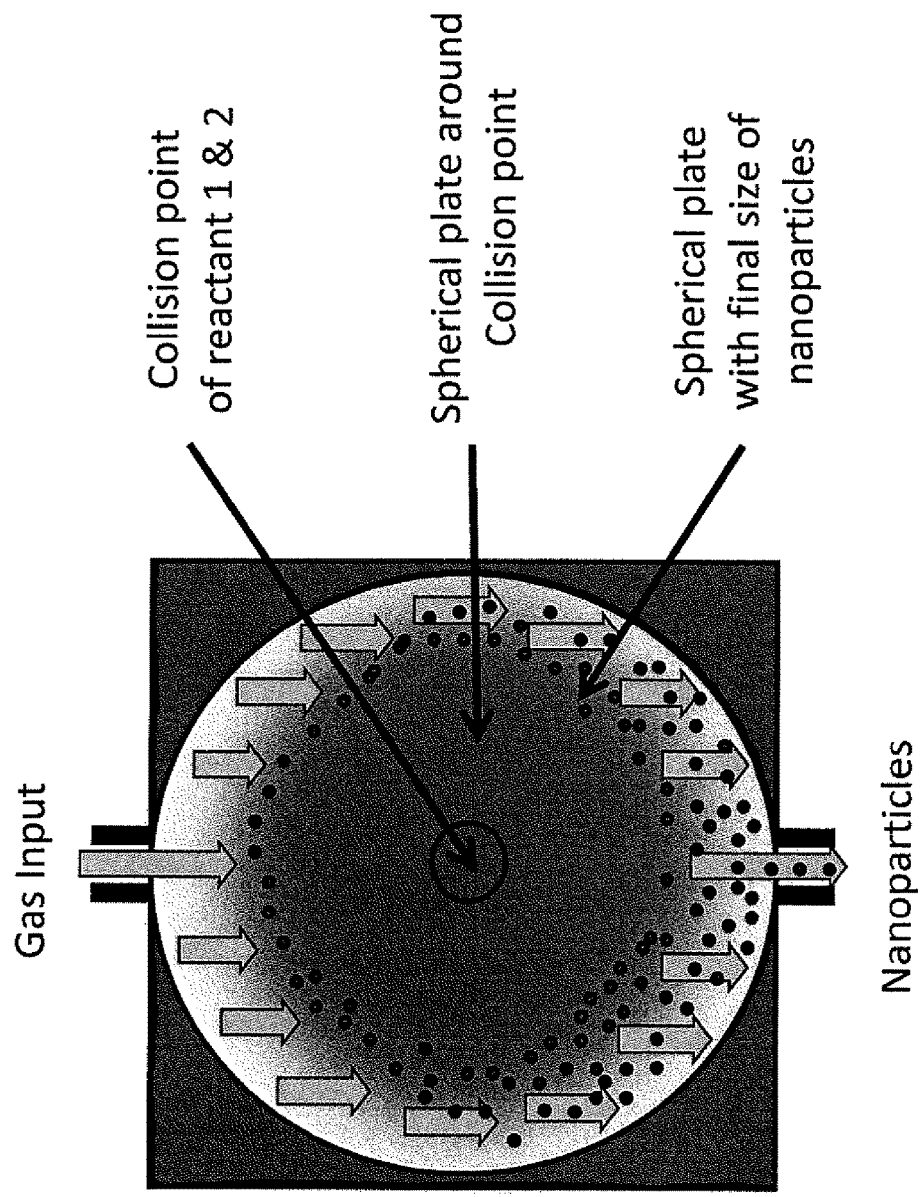
FIG. 5 is a longitudinal cross-section of the microjet reactor showing how nanoparticles grow from the collision point on the way to the edge of the spherical plate.

As shown in FIGS. 4 and 5, these two impinging jets collide in the microjet reactor in such a way as to effect precipitation at the point of collision of the jets, which, depending on the reactor geometry, form a double-disc-shaped structure there comprising fast-moving liquid jets. In the disc-edge area, very rapid mixing occurs at mixing speeds generally below 1 millisecond, frequently below 0.5 ms and mostly below 0.1 ms. As seen in FIG. 4, examples of water insoluble polymeric excipients include, but are not limited to, tocopherol, deoxycholic acid and Lipoid S 100 and combinations thereof. Also shown in FIG. 4, examples of water soluble polymeric excipients include, but are not limited to, PEG derivatives, serum albumin, PVP, polysorbate derivatives and Cremophor EL and combinations thereof. As shown in FIG. 5, nanoparticles grow from the collision point on the way to the edge of the spherical plate. Gas flows around the outer surface of the spherical plate controlling the mixing time (typically less than 0.1 ms) and with that the growth and size of the nanoparticles.

In this invention, the term "solvent" means a solvent containing one or more active target substances together with one or more auxiliary agents including, but not limited to, pharmaceutical excipients, surfactant molecules, polymers, co-polymers or block polymers.

The term "nonsolvent" also means a solvent containing one or more active target substances or auxiliary agents used to produce nanoparticles or microparticles.

These liquids may be heated or cooled, namely by an external heating means or directly in the pump, in order to dissolve the active target substance and/or the auxiliary agent, to enable the formation of nanoparticles with the desired particle size and surface properties or to stabilize the resulting molecules.

This invention includes methods of producing particles of water-soluble and water-insoluble substances in a microjet reactor and simultaneously stabilizing these either with one or more auxiliary agents or surface modifiers, the resulting particles having particle sizes of up to 2,000 nm, for example less than 1,000 nm, less than 500 nm and less than 200 nm, with polydispersion indices generally below 2.0, for example below 1.0 and further for example below 0.4.

As an alternative, another embodiment of the invention can use methods and an apparatus which allow self-organization processes in which one or more active target molecules react chemically with one or more suitable auxiliary agents that are soluble in the nonsolvent, resulting in a product that is insoluble in the solvent/nonsolvent mixture and thus permits the formation of microparticles or nanoparticles with sizes that vary according to parameters including, but not limited to, flow rate or concentration of the substances.

It is also possible to co-precipitate one or more active target substances with an insoluble reaction product of one or more auxiliary agents.

This invention furthermore can use methods of co-precipitating one or more active target substances with one or more suitable auxiliary agents in which the substance is dissolved on a molecular scale such as to form particulate systems, and provides for the surface-coating of such systems with suitable target molecules including, but not limited to, antibodies.

The solvent and nonsolvent are solutions and mixtures constituting liquid components that may contain their mass fraction in solution or in suspended form.

The solvent and nonsolvent used in this invention may be an aqueous or organic phase or a solution, mixture, emulsion or suspension, or a combination thereof.

Organic solvents of this kind may be miscible or immiscible with water. Suitable organic solvents include, but are not limited to, readily water-miscible substances such as ethanol, methanol, tetrahydrofuran, dimethylsulphoxide, acetone and 2-isopropanol, and poorly miscible substances such as toluene, hexane, heptane, pentane and methylene chloride.

Suitable auxiliary agents may be added, such as inert diluents, solubilizers, suspending agents, adjuvants, wetting agents, sweeteners, perfuming or flavouring substances, isotonic substances, colloidal dispersants and surfactants, including, but not limited to, charged phospholipids such as dimyristoylphosphatidylglycerin, algininic acid, alginates, acacia resin, gum arabic, 1,3-butylene glycol, benzalkonium chloride, colloidal silicon dioxide, cetosteryl alcohol, cetomacrogol emulsifying wax, casein, calcium stearate, cetylpyridine chloride, cetyl alcohol, cholesterol, calcium carbonate, CRODESTAS F-110, which is a mixture of sucrose stearate and sucrose distearate (Croda Inc.), clays, kaolin and bentonite, derivates of cellulose and salts thereof, such as hydroxypropyl methylcellulose (HPMC), sodium carboxymethyl cellulose, carboxymethyl cellulose and salts thereof, methyl cellulose, hydroxyethyl cellulose, hydroxypropyl cellulose, hydroxypropyl methylcellulose phtalate, non-crystalline cellulose, dicalcium phosphate, dodecyltrimethylammonium bromide, dextrane, dialkylester of sodium sulfosuccinate (e.g. AEROSEL OT, American Cyanamid), gelatine, glycerol, glycerol monostearate, glucose, p-isononylphenoxypoly (glycidol), also known as Olin 10-G or 10-GR surfactant (Olin Chemicals, Stamford, Conn.); glucamides such as octanoyl-N-methylglucamide, decanoyl-N-methylglucamide and heptanoyl-N-methylglucamide, lactose, lecithin (phosphatides), maltosides such as n-dodecyl-beta-D-maltoside, mannitol, magnesium stearate, magnesium aluminium silicates, oils such as cotton oil, seed oil, olive oil, castor oil and sesame oil; paraffin, potato starch, polyethylene glycol (e.g. CARBOWAX 3350, CARBOWAX 1450 and CARBOPOL 9340 (Union Carbide), polyoxyethylene alkyl ester (e.g. macrogolethers such as CETOMACROGOL 1000), polyoxyethylene sorbitol fatty acid esters (e.g. TWEENS, ICI Specialty Chemicals), polyoxyethylene castor oil derivatives, polyoxyethylene stearates, polyvinyl alcohol (PVA), polyvinylpyrrolidone (PVP), phosphates, 4-(1,1,3,3-tetramethylbutyl)phenol polymer with ethylene oxide and formaldehyde (also known as TYLOXAPOL, SUPERIONE and TRITON), poloxamers and polaxamines (e.g. PLURONICS F68LF, F87, F108 and TETRONIC 908, available from BASF Corporation, Mount Olive, N.J.), pyranosides such as n-hexyl-.beta.-D-glucopyranoside, n-decyl-.beta.-D-glucopyranoside, n-octyl-.beta.-D-glucopyranoside, quaternary ammonium compounds, silica, sodium citrate, starches, sorbitol esters, sodium carbonate, solid polyethylene glycols, sodium dodecyl sulfate, sodium lauryl sulfate (e.g. DUPONAL P, DuPont), stearic acid, sucrose, tapioka starch, talc, thioglucosides such as n-heptyl-.beta.-D-thioglucoside, tragacanth, triethanolamine, TRITON X-200 (Rohm and Haas); and the like.

The inert diluents, solubilizers, emulsifiers, adjuvants, wetting agents, isotonic substances, colloidal detergents and surfactants are commercially available or can be prepared by methods known to persons skilled in the art.

Certain Embodiments

In certain embodiments of the invention, the clevidipine nanoparticles were stabilized with, for example, three different approaches: In the first approach, a combination of water insoluble excipients; in the second approach, a combination of water soluble and water insoluble excipients; and, in the third approach, a combination of water soluble excipients were used for the preparation of nanoparticles. One aim for the nanoparticle preparations was to maintain the chemical stability of clevidipine and physical stability of the nanoparticles at ambient temperature and to obtain immediate release of clevidipine after administration.

According to the first aspect, clevidipine nanoparticles were stabilized with water insoluble, lipophilic excipients suitable for parenteral applications such as but not limited to vitamin E, and its derivatives, bile acid and its derivatives and phospholipid derivatives, lecithin, lysolecithin, phosphotidylserine, glycerophosphocholine, oleic acid, glycerol, inositol, diethylenetriaminepentaaceticacid, polyoxyethylene castor, polyoxyethylenehydrogenated castor oil base, polyoxyethylene sorbitan monolaurate and combinations thereof. Phospholipid derivatives were selected from a group of natural phospholipids such as the ones isolated from egg yolk for soya beans, synthetic phospholipids, phosphotadylcholine, and hydrogenated phospholipids. Bile acid derivatives were selected from a group of cholic acid, chenodeoxycholic acid, deoxycholic acid and urodeoxycholic acid. The excipients that were used, either alone or in combination for stabilization of clevidipine particles, included but were not limited to vitamin E derivatives/bile acid derivatives, vitamin E derivatives/phospholipid derivatives, bile acid derivatives/phospholipid derivatives. In order to prepare nanoparticles, clevidipine was dissolved in an organic solvent such as but not limited to ethanol, polyethylene glycol (PEG), DMSO, acetone, tetrahydrofuran, dimethylacetamide, acetonitrile, benzyl benzoate, N-methyl-2-pyrrolidone, triethanolamine, isopropanol, methanol, acetone or combinations thereof with a concentration of 0.5-200 mg/mL, for example 5-20 mg/mL and in another embodiment 5-10 mg/mL in the presence of water insoluble excipients such as vitamin E and derivatives with a concentration of 1-200 mg/mL, in another embodiment 20-50 mg/mL and in another embodiment 30-50 mg/mL and bile acid and derivatives with a concentration of 0.5-250 mg/mL, in another embodiment 5-100 mg/mL and in another embodiment 20-50 mg/mL and phospholipid derivatives with a concentration of 0.5-300 mg/mL, in another embodiment 1-100 mg/mL and in another embodiment 3-4 mg/mL. This solution was precipitated against a non-solvent for clevidipine such as but not limited to water using microjet reactor technology as recited in U.S. Pat. No. 8,697,131 and US Published Application Serial No. 2013/0012551, both of which are expressly incorporated by reference in their entireties, with a gas pressure of between 0.05-2 bar, in another embodiment 0.1-1 bar and in another embodiment 0.1-0.4 bar. Different mixing ratios of solvent containing clevidipine and excipients and aqueous non-solvent were used for the preparation of nanoparticles.

The solvent/non-solvent mixing ratios was in a range of 0.1:10-9:1, in another embodiment 0.5:9.5-1:1 and in another embodiment 0.5:9.5 to 1:5. Solvent and nonsolvent flow rates were between 0.1-2000 mL/min, in another embodiment 0.1-100 mL/min, in another embodiment 0.1-50 mL/min.

According to the second aspect of this invention, clevidipine nanoparticles were stabilized with combinations of water insoluble, lipophilic excipients suitable for parenteral applications such as but not limited to vitamin E, and its derivatives, bile acid and its derivatives and phospholipid derivatives, lecithin, lysolecithin, phosphotidylserine, glycerophosphocholine, oleic acid, glycerol, inositol, diethylenetriaminepentaaceticacid, polyoxyethylene castor, polyoxyethylenehydrogenated castor oil base, polyoxyethylene sorbitan monolaurate and a water soluble, hydrophilic excipients such as but not limited to polyethylene glycols, polypropylene glycols, bile acid salts, vitamin E TPGS, polysorbate 80, polysorbate 20, Triton X-100, lauryl glucoside, NP-40, oleyl alcohol, sorbitans (monosterate tristearate), stearyl alcohol, nonoxynols, Cremophore (RH 60 or EL), Solutol HS 15, plutonic acid, sodium dodecyl sulfate (SDS). Phospholipid derivatives were selected from a group of natural phospholipids such as the ones isolated from egg yolk or soya beans, synthetic phospholipids, phosphotadylcholine, and hydrogenated phospholipids. Bile acid derivatives were selected from a group of cholic acid, chenodeoxycholic acid, deoxycholic acid and urodeoxycholic acid or the salt derivatives of the above mentioned molecules as water soluble excipients. Different combinations of water insoluble and water soluble excipients, used for the stabilization of clevidipine nanoparticles, included but were not limited to phospholipids/bile acid salts, vitamin E/bile acid salts, vitamin E/PEG, bile acid/PEG, phospholipid/PEG, bile acid/vitamin E TPGS or phospholipid/vitamin E TPGS. In order to prepare nanoparticles, clevidipine was dissolved in an organic solvent such as but not limited to ethanol, polyethylene glycol (PEG), DMSO, acetone, tetrahydrofuran, dimethylacetamide, acetonitrile, benzyl benzoate, N-methyl-2-pyrrolidone, triethanolamine, isopropanol, methanol, acetone or combinations thereof with a concentration of 0.5-200 mg/mL, in another embodiment 5-20 mg/mL and in another embodiment 5-10 mg/mL in the presence of water insoluble excipients such as vitamin E and derivatives with a concentration of 1-200 mg/mL, in another embodiment 20-50 mg/mL and in another embodiment 30-50 mg/mL and bile acid and derivatives with a concentration of 0.5-200 mg/mL, in another embodiment 5-100 mg/mL and in another embodiment 20-50 mg/mL or phospholipid derivatives with a concentration of 0.5-250 mg/mL, in another embodiment 10-50 mg/mL and in another embodiment 20-30 mg/mL. This solution was precipitated against a nonsolvent for clevidipine such as but not limited to water in the presence of water soluble excipients such as bile acid salts with a concentration of 0.5-250 mg/mL, in another embodiment 5-100 mg/mL and in another embodiment 15-20 mg/mL, polyethylene glycol with a concentration of 0.1-100 mg/mL, in another embodiment 1-50 mg/mL in another embodiment 1-2 mg/mL or Vitamin E TPGS with a concentration of 2-30 mg/mL, in another embodiment 2.5-10 mg/mL and in another embodiment 2.5-5 mg/mL using microjet reactor technology as recited in U.S. Pat. No. 8,697,131 and US Published Application Serial No. 2013/0012551, both of which are expressly incorporated herein by reference in their entireties, with a gas pressure of between 0.05-2 bar, in another embodiment 0.1-1 bar and in another embodiment 0.1-0.4 bar. Different mixing ratios of solvent containing clevidipine and excipients and aqueous non-solvent were used for the preparation of nanoparticles. The solvent/non-solvent mixing ratios was in a range of 0.1:10-9:1, in another embodiment 0.5:9.5-1:1 and in another embodiment 0.5:9.5 to 1:5. Solvent and nonsolvent flow rates were between 0.1-2000 mL/min, in another embodiment 0.1-100 mL/min, in another embodiment 0.1-50 mL/min.

According to the third aspect of the invention, the clevidipine nanoparticles were stabilized with water soluble, hydrophilic excipients appropriate for parenteral applications such as but not limited to vitamin E TPGS, polysorbate 80, polysorbate 20, Triton X-100, lauryl glucoside, NP-40, oleyl alcohol, sorbitans (monosterate tristearate), stearyl alcohol, nonoxynols, Cremophore (RH 60 or EL), Solutol HS 15, plutonic acid, sodium dodecyl sulfate (SDS), bile acid salts, polyethylene glycol and polypropylene glycol and their combinations. Bile acid salts were selected from a group of salts of cholic acid, chenodeoxycholic acid, deoxycholic acid and urodeoxycholic acid. The excipients that were used, either alone or in combination for stabilization of clevidipine particles, included but were not limited to PEG/bile acid salts, bile acid salts/vitamin E TPGS, PEG/vitamin E TPGS. In order to prepare nanoparticles, clevidipine was dissolved in an organic solvent such as but not limited to ethanol, polyethylene glycol (PEG), DMSO, acetone, tetrahydrofuran, dimethylacetamide, acetonitrile, benzyl benzoate, N-methyl -2-pyrrolidone, triethanolamine, isopropanol, methanol, acetone or combinations thereof with a concentration of 0.5-200 mg/mL, in another embodiment 5-20 mg/mL and in another embodiment 5-10 mg/mL. This solution was precipitated against a nonsolvent for Clevidipine such as but not limited to water in the presence of water soluble excipients such as bile acid salts with a concentration of 0.5-250 mg/mL, in another embodiment 5-100 mg/mL and in another embodiment 10-20 mg/mL, polyethylene glycol with a concentration of 0.1-100 mg/mL, in another embodiment 0.5-20 mg/mL in another embodiment 0.5-1 mg/mL or Vitamin E TPGS with a concentration of 2-30 mg/mL, in another embodiment 2.5-10 mg/mL and in another embodiment 2.5-5 mg/mL using microjet reactor technology as recited in U.S. Pat. No. 8,697,131 and US Published Application Serial No. 2013/0012551, both of which are expressly incorporated herein by reference in their entireties, with a gas pressure of between 0.05-2 bar, in another embodiment 0.1-1 bar and in another embodiment 0.1-0.4 bar. Different mixing ratios of solvent containing the clevidipine and excipients and aqueous non-solvent were used for the preparation of nanoparticles. The solvent/nonsolvent mixing ratios were in a range of 0.1:10-9:1, in another embodiment 0.5:9.5-1:1 and in another embodiment 0.5:9.5 to 1:5. Solvent and non-solvent flow rates were between 0.1-2000 mL/min, in another embodiment 0.1-100 mL/min, in another embodiment 0.1-50 mL/min.

According to another aspect of the invention, production parameters of above described nanoparticles were adjusted in order to produce nanoparticles smaller than 500 nm, in another embodiment smaller than 400 nm, in another embodiment smaller than 300 nm with a PDI of smaller than 0.8, in another embodiment smaller than 0.6 in another embodiment smaller than 0.4.

According to another aspect of the invention, nanoparticles prepared as above were lyophilised in order to eliminate the solvent in the presence of cryoprotectant agents with a concentration of 1-200 mg/mL selected from a group of mono or disaccharides and polyols such as but not limited to mannitol, glycerol, propylene glycol and sucrose.

According to another aspect of the invention, removal of solvents used for nanoparticles prepared as above was realized with diafiltration.

According to another aspect of the invention, removal of solvents used for nanoparticles prepared as above was realized with dialyses.

According to another aspect of the invention, nanoparticle suspensions were autoclaved at 120° C. for 15 minutes to demonstrate stability of clevidipine nanoparticle solutions under autoclaving conditions and to render them sterile and suitable for parenteral use.

In another embodiment of the invention, it was found that the formulations were stable such that, for example, low levels of impurities were found.

Methods of Use

The clevidipine nanoparticles of the invention can be used for the treatment of, for example, hypertension when administered to a patient in need thereof. Nanoparticles disclosed herein may be combined with pharmaceutical acceptable carriers to form a pharmaceutical composition, according to another aspect of the invention. As would be appreciated by one of skill in this art, the carriers may be chosen based on the route of administration as described below, the location of the target issue, the drug being delivered, the time course of delivery of the drug, etc.

The pharmaceutical compositions of this invention can be administered to a patient by, for example, parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles of the present invention are administered to a subject in need thereof systemically, e.g., by IV infusion or injection. Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Clevidipine Nanoparticles Stabilized With Water In-Soluble Excipients

Clevidipine nanoparticles were prepared using various combinations of water insoluble excipients dissolved in the solvent as shown in Table 1. Nanoparticles were prepared using the microjet reactor technology as recited in U.S. Pat. No. 8,697,131 and US Published Application Serial No. 2013/0012551, both of which are expressly incorporated herein by reference in their entireties, at 25° C. with a nitrogen pressure of 0.1 bar. Water was used as the non-solvent for all the preparations.

TABLE 1

Compositions of clevidipine nanoparticles stabilized with water insoluble excipients

| Formulation number | Clevidipine [mg/mL] | Solvent | Vitamin E | Deoxycholic acid | Phosphotdylcholine | Flow rate Solvent solution [mL/min] | Flow rate non-solvent [mL/min] | Solvent/Non-Solvent Ratio |
|---|---|---|---|---|---|---|---|---|
| 1 | 10 | DMSO | 50.0 | 50 | — | 1.0 | 9.0 | 1:9 |
| 2 | 10 | Ethanol | 30.0 | 20 | — | 0.5 | 9.5 | 0.5:9.5 |
| 3 | 10 | Ethanol | 25.0 | — | 3.75 | 1.0 | 4.0 | 1:4 |
| 4 | 5 | Ethanol | 12.5 | — | 1.88 | 1.0 | 9.0 | 1:9 |
| 5 | 7 | DMSO/EtOH 80:20 | — | 25 | 2.00 | 1.0 | 4.0 | 1:4 |
| 6 | 7 | Ethanol | — | 50 | 2.00 | 1.0 | 9.0 | 1:9 |

Nanoparticles described in Table 1 were characterized in terms of their particle size and PDI using dynamic light scattering methodology. Results (Table 2) demonstrated that nanoparticles with different particle sizes were obtained using different combinations of water insoluble excipients.

TABLE 2

Particle size and PDI results for clevidipine nanoparticles stabilized with water insoluble excipients

| Formulation Number | Particle size (nm) | PDI |
|---|---|---|
| 1 | 192.7 | 0.094 |
| 2 | 186.2 | 0.126 |
| 3 | 586.9 | 0.524 |
| 4 | 155.2 | 0.171 |
| 5 | 216.7 | 0.063 |
| 6 | 281.6 | 0.245 |

Example 2

Clevidipine Nanoparticles Stabilized With Combination of Water In-Soluble and Water Soluble Excipients Clevidipine nanoparticles were prepared using various combinations of water in-soluble excipients dissolved in the organic solvent, and water soluble excipients dissolved in the water (non-solvent), as shown in Table 3. Nanoparticles were prepared using microjet reactor technology as recited in U.S. Pat. No. 8,697,131 and US Published Application Serial No. 2013/0012551, both of which are expressly incorporated herein by reference in their entireties, at 25° C. with a nitrogen pressure of 0.1 bar. Water was used as non-solvent for all preparations.

TABLE 3

Compositions of Clevidipine nanoparticles stabilized with a combination of water soluble and water in-soluble excipients

| | | | Water in-soluble excipients | | | Water soluble excipients | | | | | |
|---|---|---|---|---|---|---|---|---|---|---|---|
| Formulation Number | Clevidipine [mg/mL] | Solvent | Vitamin E [mg/mL] | Deoxycholic acid | Phosphotdylcholine [mg/mL] | PEG 200 [mg/mL] | Sodium deoxycholate [mg/mL] | TPGS [mg/mL] | Solvent [mL/min] | Non-Solvent [mL/min] | Solvent/Non-Solvent Ratio |
| 7 | 7 | DMSO | 30 | — | — | 1 | — | — | 0.5 | 9.5 | 0.5:9.5 |
| 8 | 10 | Ethanol | 20 | — | — | 1 | — | — | 0.5 | 9.5 | 0.5:9.5 |
| 9 | 10 | Ethanol | — | — | 30 | 1 | — | — | 1 | 9 | 1:9 |
| 10 | 8 | DMSO/Ethanol 80:20 | — | — | 48 | 1 | — | — | 1 | 1 | 1:1 |
| 11 | 7 | Ethanol | 50 | — | — | — | 50 | — | 1 | 1 | 1:1 |
| 12 | 7 | DMSO | 40 | — | — | — | 40 | — | 1 | 2 | 1:2 |
| 13 | 7 | DMSO | 40 | — | — | 1 | — | — | 1 | 9 | 1:9 |
| 14 | 7 | DMSO | 20 | — | — | 2 | — | — | 1 | 9 | 1:9 |
| 15 | 10 | Ethanol | — | 10 | — | — | — | 5 | 1 | 4 | 1:4 |
| 16 | 10 | Ethanol | — | 10 | — | — | — | 5 | 1 | 9 | 1:9 |
| 17 | 10 | Ethanol | — | — | 5 | — | — | 5 | 1 | 4 | 1:4 |
| 18 | 10 | Ethanol | — | — | 20 | — | — | 5 | 1 | 9 | 1:9 |

Nanoparticles described in Table 3 were characterized in terms of their particle size and PDI using dynamic light scattering methodology. Results shown in Table 4 demonstrated that nanoparticles with different particle sizes were obtained using different combination of water insoluble excipients and water soluble excipients.

TABLE 4

Particle size and PDI results for Clevidipine nanoparticles stabilized with a combination of water soluble and water insoluble excipients

| Formulation number | Particle size (nm) | PDI |
| --- | --- | --- |
| 7 | 229.8 | 0.083 |
| 8 | 213.1 | 0.043 |
| 9 | 196.7 | 0.470 |
| 10 | 125.0 | 0.196 |
| 11 | 243.8 | 0.276 |
| 12 | 191.3 | 0.121 |
| 13 | 329.9 | 0.094 |
| 14 | 392.4 | 0.153 |
| 15 | 153.0 | 0.042 |
| 16 | 59.99 | 0.102 |
| 17 | 90.42 | 0.094 |
| 18 | 65.48 | 0.202 |

Example 3

Clevidipine Nanoparticles Stabilized With Water Soluble Excipients

Clevidipine nanoparticles were prepared using various combinations of water soluble excipients as shown in Table 5. Nanoparticles were prepared using microjet reactor technology as recited in U.S. Pat. No. 8,697,131 and US Published Application Serial No. 2013/0012551, both of which are expressly incorporated herein by reference in their entireties, at 25° C. with a nitrogen pressure of 0.1 bar. Water was used as non-solvent for all the preparations.

TABLE 5

Compositions of clevidipine nanoparticles stabilized with water soluble excipients

| | | | Water Soluble Excipients | | | | | |
| --- | --- | --- | --- | --- | --- | --- | --- | --- |
| Formulation number | Clevidipine [mg/mL] | Solvent | PEG 200 [mg/mL] | Sodium deoxycholate [mg/mL] | TPGS [mg/mL] | Solvent [mL/min] | Non-solvent [mL/min] | Solvent/Non-Solvent Ratio |
| 19 | 10 | DMSO | — | 5 | 2.5 | 1 | 5 | 1:5 |
| 20 | 10 | DMSO | — | 5 | 5 | 1 | 5 | 1:5 |
| 21 | 5 | DMSO | — | 5 | 2.5 | 1 | 4 | 1:4 |
| 22 | 5 | DMSO | — | 2.5 | 2.5 | 1 | 4 | 1:4 |
| 23 | 10 | Ethanol | — | 10 | 2.5 | 1 | 9 | 1:9 |
| 24 | 10 | Ethanol | — | 5 | 5 | 1 | 2 | 1:2 |
| 25 | 10 | DMSO | 1 | — | 2.5 | 1 | 9 | 1:9 |
| 26 | 10 | DMSO | 0.5 | — | 5 | 1 | 2 | 1:2 |
| 27 | 10 | Ethanol | 1 | 10 | — | 0.5 | 9.5 | 0.5:9.5 |
| 28 | 10 | DMSO | 1.5 | 5 | — | 0.5 | 9.5 | 0.5:9.5 |

Nanoparticles described in Table 5 were characterized in terms of their particle size and PDI using dynamic light scattering methodology. The results shown in Table 6 demonstrate that nanoparticles with different particle sizes were obtained using different combinations of water soluble excipients.

TABLE 6

Particle size and PDI results for clevidipine nanoparticles stabilized with water soluble excipients

| Example number | Particle size (nm) | PDI |
| --- | --- | --- |
| 19 | 211.2 | 0.007 |
| 20 | 216.3 | 0.170 |
| 21 | 209.6 | 0.027 |
| 22 | 155.5 | 0.023 |
| 23 | 371.1 | 0.151 |
| 24 | 196.4 | 0.095 |
| 25 | 101.0 | 0.140 |
| 26 | 65.95 | 0.084 |
| 27 | 228.6 | 0.273 |
| 28 | 400.2 | 0.012 |

Example 4

Stability of Certain Clevidipine Nanoparticles Prior to Solvent Removal

The stability of nanoparticle suspensions was evaluated before the solvent removal. Three representative formulations were selected and evaluated for stability in solvent/non-solvent mixtures for 96 hours. Particle size, PDI and clevidipine assay determinations were conducted every 24 hours. It was found that the nanoparticles of Examples 7 and 9 were stable for 96 hours while the nanoparticles of Example 2 were stable for 96 hours.

TABLE 7

Particle size, PDI and Assay results for certain nanoparticle formulations

| Formulation number | t = 0 | t = 24 h | t = 48 h | t = 72 h | t = 96 h |
|---|---|---|---|---|---|
| | | | Particle size (nm) | | |
| 2 | 219.90 | 222.20 | 231.30 | 231.80 | 232.00 |
| 7 | 226.80 | 228.20 | 230.90 | 230.70 | 227.00 |
| 9 | 93.53 | 93.39 | 94.05 | 95.14 | 96.00 |
| | | | PDI | | |
| 2 | 0.09 | 0.18 | 0.11 | 0.13 | 0.20 |
| 7 | 0.02 | 0.03 | 0.03 | 0.01 | 0.07 |
| 9 | 0.20 | 0.20 | 0.19 | 0.24 | 0.26 |
| | | | Assay (%) | | |
| 2 | 100.00 | 98.90 | 100.20 | 98.20 | 98.63 |
| 7 | 100.00 | 100.71 | 99.77 | 97.31 | 90.72 |
| 9 | 100.00 | 101.70 | 101.93 | 98.38 | 100.01 |

Example 5

Stability of Certain Clevidipine Nanoparticles After Autoclaving

Selected formulations were lyophilised with the following program for the removal of the organic solvent.

TABLE 8

Lyophilization program for certain nanoparticle formulations

| | | | | | Process | | | | | |
|---|---|---|---|---|---|---|---|---|---|---|
| Loading | Freezing | | Primary drying | | | | | | Secondary drying | |
| | | | | | Step | | | | | |
| 1 | 2 | 3 | 4 | 5 | 6 | 7 | 8 | 9 | 10 |
| Time [h:m] | — | 18:00 | 0:01 | 6:30 | 4:30 | 4:00 | 1:00 | 4:00 | 0:01 | 30:00 |
| Storage space temp. [° C.] | 20 | −85 | −30 | −30 | 20 | 20 | 30 | 30 | 30 | 30 |
| Vacuum [mbar] | | | 0.12 | 0.12 | 0.12 | 0.12 | 0.12 | 0.12 | 0.001 | 0.001 |

After lyophilization, process nanoparticles were reconstituted in distilled water and autoclaved at 121° C. for 15 minutes to determine the stability of nanoparticle formulations following the autoclaving process. The physical stability results are provided in Table 9 and chemical stability results are provided in Table 9.

TABLE 9

Particle size and PDI results before and after autoclaving

| Formulation number | Before autoclave | After autoclave |
|---|---|---|
| | Zeta potential [mV] | |
| 2 | −36.1 | −35.9 |
| 9 | −37.5 | −32.6 |
| 7 | −22.4 | −21.8 |
| | Particle size [nm] | |
| 2 | 182.6 | 179.0 |
| 9 | 308.2 | 305.6 |
| 7 | 260.6 | 267.3 |
| | PDI | |
| 2 | 0.030 | 0.143 |
| 9 | 0.158 | 0.178 |
| 7 | 0.083 | 0.031 |

TABLE 10

Results for impurity analyses after autoclaving

| Formulation number | Area Total Impurity | Theoretical Clevipidine con. [mg/mL] | Total Impurity [%] |
|---|---|---|---|
| 2 | not detected | 0.125 | 0 |
| 9 | 574027 | 0.250 | 1.033 |
| 7 | 819051 | 0.500 | 0.737 |

There was no change in particle size and PDI values of the nanoparticles during autoclaving. Example 2 showed no change in the impurity profile after the autoclaving process, while there was an increase in the impurity content of formulations 9 and 7. Based on this information, the lyophilization process was adjusted to decrease the stress on nanoparticle formulations during the freezing process which also affects the stability of the samples during the autoclaving process.

The following lyophilization process was used in the second trials.

TABLE 11

Adjusted Lyophilization program for certain nanoparticle formulations

| | Loading | Freezing | Primary drying | | | | | | Secondary drying | |
|---|---|---|---|---|---|---|---|---|---|---|
| Step | 1 | 2 | 3 | 4 | 5 | 6 | 7 | 8 | 9 | 10 |
| Time [h:m] | — | 18:00 | 0:01 | 6:30 | 4:30 | 4:00 | 1:00 | 4:00 | 0:01 | 30:00 |
| Storage space temperature | 20 | -30 | -30 | -30 | 20 | 20 | 30 | 30 | 30 | 30 |
| Vacuum [mbar] | | | 0.12 | 0.12 | 0.12 | 0.12 | 0.12 | 0.12 | 0.001 | 0.001 |

After the lyophilization process, nanoparticles were reconstituted in distilled water and autoclaved at 121° C. for 15 minutes to determine the stability of nanoparticle formulations through the autoclaving process. A comparison of the chemical stability of autoclaved nanoparticles, reconstituted following the initial and adjusted lyophilization cycles, is provided in Table 12. Results indicate that the adjusted lyophilization process improved the stability of nanoparticles through the autoclaving process.

TABLE 12

Comparison of impurity levels of the autoclaved samples produced with initial and adjusted lyophilization method

| Formulation number | Total Impurity [%] Initial lyophilization method | Total Impurity [%] adjusted lyophilization method |
|---|---|---|
| 2 | 0 | 0 |
| 9 | 1.033 | 0.17 |
| 7 | 0.737 | 0 |

Example 6

Evaluation of Stability of Certain Nanoparticles Under Accelerated Storage Condition Accelerated stability studies were conducted with the selected formulations for 2 weeks at 40° C., and the samples were analyzed for impurity levels to determine the chemical stability of the nanoparticles. As shown in Table 13, all nanoparticle formulations were chemically stable for 2 weeks under accelerated conditions.

TABLE 13

Comparison of impurity levels of the certain nanoparticle prototypes under accelerated conditions

| Formulation number | Total Impurity [%] |
|---|---|
| 2 t = 0 | 0.00 |
| 9 t = 0 | 0.17 |
| 7 t = 0 | 0.00 |
| 2 t = 1 week | 0.00 |
| 9 t = 1 week | 0.27 |
| 7 t = 1 week | 0.00 |
| 2 t = 2 weeks | 0.37 |
| 9 t = 2 weeks | 0.36 |
| 7 t = 2 weeks | 0.23 |

Example 7

A comparison of the chemical stability of autoclaved nanoparticles reconstituted following adjusted lyophilization cycle and the clevidipine emulsion is provided in Table 14. Results indicate that clevidipine in the nanoparticles demonstrated improved chemical stability through the autoclaving process than in the emulsion.

TABLE 14

Comparison of impurity levels of the autoclaved samples of certain nanoparticle prototypes with that of Clevidipine emulsion

| Formulation number | Total Impurity [%] |
|---|---|
| 2 | 0.00 |
| 9 | 0.17 |
| 7 | 0.00 |
| Clevidipine emulsion Lot A | 1.1 |
| Clevidipine emulsion Lot B | 1.3 |
| Clevidipine emulsion Lot C | 1.4 |

Example 8

Evaluation of In-Vitro Metabolism

The in-vitro release from selected nanosuspension formulations was evaluated in whole human blood and compared with that of the reference Cleviprex emulsion (commercial product).

Figure 6:
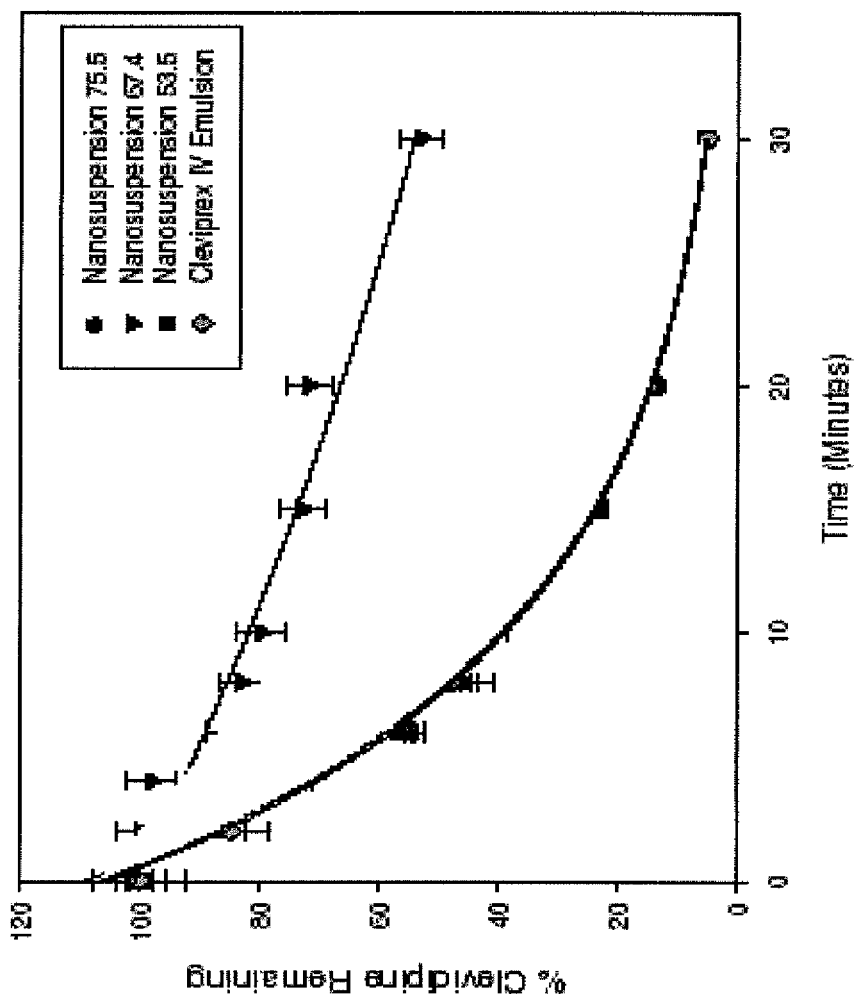
FIG. 6 is a graph comparing the kinetics of metabolism of clevidipine nanoparticle formulations of the invention with that of reference product clevidipine emulsion.

Samples of whole human blood were individually spiked with aliquots of the nanosuspension prototypes and Cleviprex emulsion, respectively, and then evaluated for clevidipine content via LC/MS/MS. The time course profiles for clevidipine decline in the test and reference formulations are provided in FIG. 6. The results demonstrate that clevipidine declined exponentially for all formulations. Elimination profiles for nanosuspensions in formulation 7 and 2 were essentially superimposable with that of Cleviprex emulsion while that of formulation 9 was slower. The apparent elimination rate constant (λ) was obtained as a slope of exponential decay and the apparent half-life was calculated as ln(2)/λ. and the data are provided in Table 15.

TABLE 15

Comparison of apparent half-life of
certain nanoparticle formulations
with that of Clevidipine emulsion

| Formulation number | T ½ (min) |
|---|---|
| 2 | 6.89 |
| 9 | 33.38 |
| 7 | 6.96 |
| Clevidipine Emulsion | 7.96 |

Clevidipine emulsion was shown to have a half-life of 7.96 minutes. The half-lives of the nanoparticle formulations in formulation 2 and 7 were found to be quite comparable, which was surprising given that these formulations were prepared with water insoluble excipients. Formulation 9 was prepared with a combination of water soluble excipients and insoluble excipients and, here, surprisingly slower kinetics were observed in comparison to the reference product.

Example 9

Additional Clevidipine Nanoparticles Stabilized With Water In-Soluble Excipients Clevidipine nanoparticles were prepared using various combinations of water insoluble excipients dissolved in the solvent as shown in Table 16. Nanoparticles were prepared using the microjet reactor technology as recited in U.S. Pat. No. 8,697,131 and US Published Application Serial No. 2013/0012551, both of which are expressly incorporated herein by reference in their entireties, at 25° C. with a nitrogen pressure of 0.1 bar. Water was used as the non-solvent for all the preparations.

Nanoparticles described in Table 16 were characterized in terms of their particle size and PDI using dynamic light scattering methodology. Results (Table 17) demonstrated that nanoparticles with different particle sizes were obtained using different combinations of water insoluble excipients:

TABLE 17

Particle Size and PDI for Clevidipine Nanoparticles
Prepared with Water Insoluble Excipients

| Formulation number | Particle size (nm) | PDI |
|---|---|---|
| 29 | 112.0 | 0.074 |
| 30 | 152 | 0.132 |
| 31 | 150.6 | 0.130 |
| 32 | 110.4 | 0.072 |
| 33 | 116.4 | 0.156 |
| 34 | 138.2 | 0.118 |
| 35 | 104.9 | 0.082 |
| 36 | 72.7 | 0.128 |
| 37 | 93.8 | 0.086 |
| 38 | 134.8 | 0.097 |
| 39 | 119.2 | 0.165 |

Example 10

Additional Clevidipine Nanoparticles Stabilized With Combination of Water In-Soluble and Water Soluble Excipients Clevidipine nanoparticles were prepared using various combinations of water in-soluble excipients dissolved in the organic solvent, and water soluble excipients dissolved in the water (non-solvent), as shown in Table 18. Nanoparticles were prepared using microjet reactor technology as recited in U.S. Pat. No. 8,697,131 and US Published Application Serial No. 2013/0012551, both of which are expressly incorporated herein by reference in their entireties, at 25° C. with a nitrogen pressure of 0.1 bar. Water was used as non-solvent for all preparations.

TABLE 16

Precipitation Conditions and Compositions of Clevidipine Nanoparticles
Prepared with Water Insoluble Excipients

| Form. number | Clevidipine [mg/mL] | Solvent | Concentration of Water insoluble Excipients (mg/mL) | | | Flow rate Solvent [mL/min] | Flow rate Non-solvent [mL/min] | Solvent/ Non-Solvent Ratio |
|---|---|---|---|---|---|---|---|---|
| | | | Vitamin E | Deoxycholic acid | Phosphotdyl-choline | | | |
| 29 | 5 | Ethanol | 20 | 30 | — | 2.5 | 50 | 1:20 |
| 30 | 7.5 | Ethanol | 20 | 10 | — | 2.5 | 50 | 1:20 |
| 31 | 5 | Ethanol | 20 | 10 | — | 5 | 50 | 1:10 |
| 32 | 7.5 | Ethanol | 20 | 10 | — | 7.5 | 50 | 1.5:10 |
| 33 | 7.5 | Ethanol | 30 | 50 | — | 5 | 50 | 1:10 |
| 34 | 7.5 | Ethanol | 30 | 30 | — | 2.5 | 50 | 1:20 |
| 35 | 7.5 | Ethanol | 20 | 30 | — | 5 | 50 | 1:10 |
| 36 | 7.5 | Ethanol | 20 | 50 | — | 2.5 | 50 | 1:20 |
| 37 | 7.5 | Ethanol | 30 | 30 | — | 5 | 50 | 1:10 |
| 38 | 7.5 | Ethanol | 30 | 10 | — | 5 | 50 | 1:10 |
| 39 | 8.2 | Ethanol | 19.9 | 25.2 | — | 7.5 | 50 | 1:10 |

TABLE 18

Precipitation Conditions and Compositions of Clevidipine Nanoparticles
Prepared with Combination of Water Soluble and Water Insoluble Excipients

| | | | Water in-soluble excipients | | | Water soluble excipients | | | | | |
|---|---|---|---|---|---|---|---|---|---|---|---|
| Form. No. | Clevidipine [mg/mL] | Solvent | Vitamin E [mg/mL] | Deoxy-cholic acid [mg/mL] | Phosphotdyl-choline [mg/mL] | Tween 20 [mg/mL] | Kolliphor EL [mg/mL] | Kolliphor RH 40 [mg/mL] | Solvent [mL/min] | Non-solvent [mL/min] | Solvent/Non-Solvent Ratio |
| 40 | 2.5 | EtOH | 30 | 10 | — | 0.025 | | | 5 | 50 | 1:10 |
| 41 | 2.5 | EtOH | 50 | 10 | — | 0.025 | | | 5 | 50 | 1:10 |
| 42 | 2.5 | EtOH | 30 | 10 | — | | 0.025 | | 5 | 50 | 1:10 |
| 43 | 2.5 | EtOH | 50 | 10 | — | | 0.025 | | 5 | 50 | 1:10 |
| 44 | 2.5 | EtOH | 30 | 10 | — | | | 0.025 | 5 | 50 | 1:10 |
| 45 | 2.5 | EtOH | 30 | 10 | — | 0.025 | | | 10 | 50 | 2:10 |
| 46 | 2.5 | EtOH | 30 | 10 | — | | 0.025 | | 10 | 50 | 2:10 |

Nanoparticles described in Table 18 were characterized in terms of their particle size and PDI using dynamic light scattering methodology. Results shown in Table 19, below, demonstrated that nanoparticles with different particle sizes were obtained using different combination of water insoluble excipients and water soluble excipients.

TABLE 19

Particle Size and PDI Results for Clevidipine Nanoparticles Prepared with a Combination of Water Soluble and Water Insoluble excipients.

| Formulation number | Particle size (nm) | PDI |
|---|---|---|
| 40 | 192.7 | 0.207 |
| 41 | 195.6 | 0.153 |
| 42 | 178.2 | 0.137 |
| 43 | 196.8 | 0.111 |
| 44 | 175.6 | 0.201 |
| 45 | 210.4 | 0.137 |
| 46 | 205.9 | 0.102 |

Example 11

Solvent Removal via Diafiltration

Solvent removal was also evaluated via Diafiltration using a molecular permeable filter and exchange medium containing either an ionic or a non-ionic surfactant. During diafiltration, fresh exchange medium was added to the retentate at the same rate as filtrate is generated to facilitate the process. A summary of diafiltration process and results are provided in Tables 20 and 21 respectively for exchange medium containing ionic and non-ionic surfactants.

TABLE 20

Diafiltration Results for Exchange Medium containing Ionic Surfactant

| | |
|---|---|
| Membrane | MJR-M-21 70 kd |
| Medium for constant diafiltration | 1 mg/mL Na Deoxycholate |
| Volume exchange | 10 times |
| Formulation | 10 |
| Before diafiltration | |
| pH value | 4,651 |
| Clevidipine starting conc. [µg/mL] | 527.72 |
| Particle size [nm] | 123.1 |
| PDI | 0.227 |
| After diafiltration | |
| Recovery assay [%] | 93.3 |
| pH value | 6.993 |
| Clevidipine conc. [µg/mL] | 361.98 |
| Particle size [nm] | 102.7 |
| PDI | 0.167 |

TABLE 21

Diafiltration Results for Exchange Medium containing Non-Ionic Surfactants

| Membrane | | | | | | | |
|---|---|---|---|---|---|---|---|
| MJR-M-21 70 kd | MJR-M-21 70 kd | MJR-M-21 70 kd | MJR-M-21 70 kd | MJR-M-21 70 kd | MJR-M-21 70 kd | MJR-M-21 70 kd |
| Medium for constant diafiltration | | | | | | | |
| 0.025 mg/mL Tween 20 | 0.025 mg/mL Tween 20 | 0.025 mg/mL Kolliphor EL | 0.025 mg/mL Kolliphor EL | 0.025 mg/mL Kolliphor RH40 | 0.025 mg/mL Tween 20 | 0.025 mg/mL Kolliphor EL |
| Volume exchange | | | | | | | |
| 5 times | 5 times | 5 times | 5 times | 5 times | 5 times | 5 times |
| Formulation | | | | | | | |
| 40 | 41 | 42 | 43 | 44 | 45 | 46 |

| | | | Before diafiltration | | | | |
|---|---|---|---|---|---|---|---|
| pH value | 4.752 | 5.843 | 5.454 | 5.885 | 5.781 | 4.952 | 5.056 |
| Clevidipine starting conc. [µg/mL] | 230.8 | 227.4 | 221.3 | 235.7 | 206.5 | 485.6 | 475.6 |
| Particle size [nm] | 192.7 | 195.6 | 178.2 | 196.8 | 175.6 | 210.4 | 205.9 |
| PDI | 0.207 | 0.153 | 0.137 | 0.111 | 0.201 | 0.137 | 0.102 |
| ZETA potential [mV] | −29.1 | −29.3 | −30.3 | −31.3 | −29.4 | −31.5 | −30.8 |
| | | | After diafiltration | | | | |
| Recovery assay [%] | 99.7 | 101.3 | 99.9 | 99.4 | 100.2 | 100.6 | 101.8 |
| pH value | 4.479 | 5.194 | 4.803 | 5.316 | 4.759 | 5.085 | 5.293 |
| Clevidipine conc. [µg/mL] | 255.8 | 265.9 | 245.6 | 270.4 | 228.7 | 505.4 | 500.9 |
| Particle size [nm] | 185.4 | 197.3 | 182.5 | 201.7 | 180.6 | 211.9 | 202.7 |
| PDI | 0.108 | 0.096 | 0.182 | 0.167 | 0.152 | 0.127 | 0.207 |
| ZETA potential [mV] | −32.4 | −27.6 | −31.6 | −29.7 | −30.3 | −28.7 | −31.9 |

No significant change was observed in the particle size for all of the formulations. Furthermore the assay recoveries for all the formulations were higher than 99% demonstrating that the diafiltration process can successfully remove residual solvents without impacting the physicochemical stability of the nanoparticles.

Example 12

Evaluation of Freeze-Thaw Stability of Selected Nanoparticles

Selected nano-supension formulations were subjected to freeze-thaw cycling following diafiltration and their physicochemical stability was evaluated after each freeze-thaw cycle. The nanoparticles were frozen at −20° C. for 8 or 12 hours and thawed at room temperature for 12 hours for each cycle. The compositions of nanoparticles containing clevidipine used for the freeze-thaw stability study are provided in Tables 22. Results of freeze-thaw stability are provided in Tables 23 and 24 respectively for nanoparticles prepared with ionic and non-ionic surfactants. Several nanoparticle formulations including formulations 47, 49, 54, 56, 57-63 showed no significant change in assay and particle size values after three freeze thaw cycles indicating potential long-term physical stability of for these formulations.

TABLE 22

Compositions of Nanoparticle Formulations used for Freeze-thaw Stability Evaluation

| ID | Clevidipine (mg/ml) | Vit E (mg/ml) | Deoxycholic acid (mg/ml) | Sodium Deoxycholate (mg/ml) | Tween 20 (mg/mL) | Kolliphor RH 40 (mg/mL) | Kolliphor EL (mg/mL) | pH Pre-Diafiltration | pH post diafiltration |
|---|---|---|---|---|---|---|---|---|---|
| 47 | 0.24 | 0.95 | 1.43 | 1 | 0 | 0 | 0 | | |
| 48 | 0.36 | 0.95 | 0.48 | 1 | 0 | 0 | 0 | 4.65 | 6.93 |
| 48 | 0.45 | 1.82 | 0.91 | 1 | 0 | 0 | 0 | 4.61 | 7.0 |
| | | | | | | | | 4.67 | |
| 50 | 0.98 | 2.61 | 1.30 | 1 | 0 | 0 | 0 | | |
| 51 | 0.68 | 2.73 | 4.55 | 1 | 0 | 0 | 0 | 4.43 | 6.83 |
| 52 | 0.36 | 1.43 | 1.43 | 1 | 0 | 0 | 0 | 4.62 | 7.08 |
| 53 | 0.68 | 1.82 | 2.73 | 1 | 0 | 0 | 0 | 4.49 | 7.06 |
| 54 | 0.36 | 0.95 | 2.38 | 1 | 0 | 0 | 0 | 4.49 | 6.79 |
| 55 | 0.68 | 1.82 | 2.73 | 1 | 0 | 0 | 0 | | |
| 56 | 0.68 | 2.73 | 0.91 | 1 | 0 | 0 | 0 | 4.54 | 6.87 |
| 57 | 0.23 | 2.73 | 0.91 | 0 | 0.023 | 0 | 0 | 4.75 | 4.48 |
| 58 | 0.23 | 4.55 | 0.91 | 0 | 0.023 | 0 | 0 | 5.84 | 5.19 |
| 59 | 0.23 | 2.73 | 0.91 | 0 | 0 | 0 | 0.023 | 5.45 | 4.80 |
| 60 | 0.23 | 4.55 | 0.91 | 0 | 0 | 0 | 0.023 | 5.89 | 5.33 |
| 61 | 0.23 | 2.73 | 0.91 | 0 | 0 | 0.023 | 0 | 5.78 | 4.76 |
| 62 | 0.42 | 5 | 1.67 | 0 | 0.021 | 0 | 0 | 4.55 | 5.09 |
| 63 | 0.42 | 5 | 1.67 | 0 | 0 | 0 | 0.021 | 5.06 | 5.29 |

TABLE 23

Results of Freeze-Thaw Cycling for Nanoparticle Formulations Prepared with Ionic Surfactants

| | t0 | | | First cycle | | | Second cycle | | | Third cycle | | |
|---|---|---|---|---|---|---|---|---|---|---|---|---|
| No. | Particle size (nm) | PDI | Assay (µg/mL) | Particle size (nm) | PDI | Assay (%) | Particle size (nm) | PDI | Assay (%) | Particle size (nm) | PDI | Assay (%) |
| 47 | 112 | 0.074 | 206.0 | 113.2 | 0.103 | 99.9 | 112.19 | 0.228 | 100.4 | 110.68 | 0.253 | 99.7 |
| 48 | 152 | 0.132 | 335.5 | 149.9 | 0.102 | 98.5 | 134.6 | 0.181 | 76.2 | 118.9 | 0.212 | 63.4 |
| 49 | 150.6 | 0.130 | 436.9 | 153.6 | 0.197 | 98.6 | 147 | 0.155 | 99.5 | 136.1 | 0.180 | 99.0 |
| 50 | 110.4 | 0.072 | 739.6 | 113.3 | 0.099 | 11.3 | 111 | 0.391 | 11.4 | 122.1 | 0.307 | 10.7 |
| 51 | 116.4 | 0.156 | 524.5 | 119.3 | 0.178 | 2.5 | 189.8 | 0.422 | 3.2 | 386.5 | 0.749 | 3.1 |
| 52 | 138.2 | 0.118 | 262.2 | 135.73 | 0.097 | 61.9 | 135.12 | 0.154 | 61.2 | 136.81 | 0.208 | 56.0 |
| 53 | 104.9 | 0.082 | 765.9 | 112.3 | 0.129 | 4.7 | 211.1 | 0.484 | 4.6 | 244.8 | 0.513 | 4.5 |
| 54 | 72.7 | 0.128 | 182.4 | 76.75 | 0.089 | 99.0 | 74.9 | 0.160 | 99.6 | 76.2 | 0.203 | 101.8 |
| 55 | 93.8 | 0.086 | 430.7 | 118.3 | 0.126 | 7.4 | 280.4 | 0.584 | 7.6 | 228 | 0.469 | 7.2 |
| 56 | 134.8 | 0.097 | 616.4 | 133.2 | 0.111 | 99.8 | 134.1 | 0.107 | 100.1 | 134.5 | 0.153 | 100.2 |

TABLE 24

Results of Freeze-Thaw Cycling for Nanoparticle Formulations Prepared with Non-Ionic Surfactants

| | t0 | | | First cycle | | | Second cycle | | | Third cycle | | |
|---|---|---|---|---|---|---|---|---|---|---|---|---|
| No. | Particle size (nm) | PDI | Assay (µg/mL) | Particle size (nm) | PDI | Assay (%) | Particle size (nm) | PDI | Assay (%) | Particle size (nm) | PD1 | Assay (%) |
| 57 | 192.7 | 0.207 | 255.8 | 192.2 | 0.102 | 99.1 | 198.4 | 0.172 | 99.5 | 195.4 | 0.202 | 99.3 |
| 58 | 195.6 | 0.153 | 265.9 | 198.7 | 0.167 | 98.9 | 225.6 | 0.110 | 95.6 | 259.1 | 0.184 | 93.1 |
| 59 | 178.2 | 0.137 | 245.6 | 169.2 | 0.207 | 99.6 | 182.5 | 0.167 | 98.7 | 185.1 | 0.106 | 99.2 |
| 60 | 196.8 | 0.111 | 270.4 | 202.4 | 0.163 | 99.5 | 193.8 | 0.149 | 99.9 | 201.7 | 0.119 | 99.1 |
| 61 | 175.6 | 0.201 | 238.7 | 186.7 | 0.182 | 99.6 | 200.7 | 0.173 | 92.8 | 227.3 | 0.167 | 90.7 |
| 62 | 210.4 | 0.137 | 505.4 | 210.5 | 0.07 | 99.4 | 206.7 | 0.192 | 99.8 | 212.9 | 0.161 | 99.4 |
| 63 | 205.9 | 0.102 | 500.9 | 208.9 | 0.118 | 99.3 | 205.1 | 0.134 | 99.8 | 207.3 | 0.181 | 99.3 |

Example 13

Evaluation of Stability of Selected Nanoparticles

Stability studies were conducted with the selected formulations at long term (25° C.) and accelerated storage conditions (40° C.) for 3 months, to determine the long term physico-chemical stability of the nanoparticles. The compositions of nanoparticle formulations used for the stability studies are summarized in Table 25:

TABLE 25

Summary of Nanoparticle Compositions used for Stability Study

| No. | Clevidipine (mg/mL) | Vitamin E (mg/mL) | Deoxycholic acid (mg/mL) | Sodium Deoxycholate (mg/mL)] |
|---|---|---|---|---|
| 64 | 0.5 | 2 | 3 | 1 |
| 65 | 0.5 | 2 | 1 | 1 |
| 66 | 0.5 | 1.33 | 3.33 | 1 |
| 67 | 0.5 | 2 | 0.67 | 1 |
| 68 | 0.5 | 1.25 | 1.56 | 1 |

The physical stability data (particle size and PDI) are provided in Table 26 and Table 27 respectively for nanoparticles stored at 25° C. and 40° C. There was no change in particle size change for the formulations 65 and 67 for 3 months at both temperatures while the remaining nanoparticle formulations demonstrated agglomeration after two months of storage.

TABLE 26

Particle Size and PDI Results before and after Storage at 25° C. 60% RH

| | 0 months | | 1 months | | 2 months | | 3 months | |
|---|---|---|---|---|---|---|---|---|
| No. | Particle size (nm) | PDI | Particle size (nm) | PDI | Particle size (nm) | PDI | Particle size (nm) | PDI |
| 64 | 117.9 | 0.204 | 122.8 | 0.185 | agglomeration | | agglomeration | |
| 65 | 145.6 | 0.127 | 140.2 | 0.164 | 132.7 | 0.219 | 135.8 | 0.186 |
| 66 | 82.4 | 0.137 | 80.3 | 0.172 | agglomeration | | agglomeration | |
| 67 | 130.5 | 0.234 | 121.9 | 0.204 | 127.6 | 0.153 | 120.9 | 0.219 |
| 68 | 119.2 | 0.165 | 121.8 | 0.149 | agglomeration | | agglomeration | |

TABLE 27

Particle Size and PDI Results before and after Storage at 40° C. 70% RH

| No. | t0 months Particle size (nm) | PDI | t1 months Particle size (nm) | PDI | t2 months Particle size (nm) | PDI | t3 months Particle size (nm) | PDI |
|---|---|---|---|---|---|---|---|---|
| 64 | 117.9 | 0.204 | 121.4 | 0.104 | agglomeration | | agglomeration | |
| 65 | 145.6 | 0.127 | 141.9 | 0.201 | 147.5 | 0.186 | 141.6 | 0.109 |
| 66 | 82.4 | 0.137 | 76.4 | 0.209 | agglomeration | | agglomeration | |
| 67 | 130.5 | 0.234 | 122.9 | 0.157 | 125.4 | 0.111 | 123.7 | 0.205 |
| 68 | 119.2 | 0.165 | 127.6 | 0.163 | agglomeration | | agglomeration | |

The potency data for nanoparticle stored at 25° C. and 40° C. condition are provided in Table 28. Assay determination was not conducted for certain formulations after 2 months due to agglomeration of the samples. The assay values for nanoparticle formulations 65 and 67 were higher than 95% at the end of 3 months at both temperatures and were therefore stable over a time period of 3 months.

TABLE 28

Assay Results before and after Storage at 25° C. 60% RH and 40° C./75% RH

| No. | Initial (Time 0) assay (µg/mL) | Assay (%) at 25° C./60% RH 1 Month | 2 Months | 3 Months | Assay (%) at 40° C./75% RH 1 Month | 2 Months | 3 Months |
|---|---|---|---|---|---|---|---|
| 64 | 503.6 | 95.7 | ND | | 94.2 | ND | |
| 65 | 495.6 | 99.6 | 98.1 | 97.6 | 99.1 | 95.6 | 96.3 |
| 66 | 507.1 | 93.4 | ND | | 91.8 | ND | |
| 67 | 486.3 | 99.2 | 97.7 | 96.3 | 99.2 | 97.1 | 95.3 |
| 68 | 493.1 | 99.4 | ND | | 98.4 | ND | |

ND—Not Determined

Samples were analyzed using reversed phase high performance liquid chromatography with UV-detection at 220 nm. Summary of degradation products formed during storage of nanoparticle at 25° C. and 40° C. condition are provided in Table 29. Certain formulations were not analyzed after 1 month due to agglomeration. In general degradation of clevidipine was observed during storage, which was consistent with its known degradation mechanism.

Clevidipine hydrolyzed to the corresponding acid H152/81, followed by subsequent decarboxylation to H168/79 to an extent of about 1.5% or less over the period of 3 month storage. In addition, clevidipine was also oxidized to form its pyridine analog H324/78. This could be potentially minimized by implementing adequate controls to minimize oxygen exposure to clevidipine during preparation as well as upon storage of nanoparticles.

TABLE 29

Summary of Impurity Results on Storage at 25° C. 60% RH and 40° C./75% RH

| Individual impurities | RT/min | RRT | Formulation No. 67 initial | 25° C.-1 m | 25° C.-2 m | 25° C.-3 m | 40° C.-1 m | 40° C.-2 m | 40° C.-3 m | Formulation No. 65 initial | 25° C.-1 m | 25° C.-2 m | 25° C.-3 m | 40° C.-1 m | 40° C.-2 m |
|---|---|---|---|---|---|---|---|---|---|---|---|---|---|---|---|
| H152/81 | 11.5 | 0.71 | 0.000 | 0.341 | 0.438 | 0.290 | 0.336 | 0.599 | 0.841 | 0.000 | 0.115 | 0.155 | 0.289 | 0.089 | 1.215 |
| S24 or S25 | 13.5 | 0.83 | 0.000 | 0.000 | 0.000 | 0.025 | 0.000 | 0.000 | 0.026 | 0.000 | 0.000 | 0.000 | 0.038 | 0.017 | 0.000 |
| S23 | 13.9 | 0.85 | 0.000 | 0.000 | 0.000 | 0.022 | 0.163 | 0.000 | 0.049 | 0.000 | 0.000 | 0.000 | 0.029 | 0.032 | 0.000 |
| unknown 1 | 14.4 | 0.88 | 0.000 | 0.000 | 0.000 | 0.000 | 0.000 | 0.000 | 0.076 | 0.000 | 0.000 | 0.000 | 0.000 | 0.000 | 0.000 |
| H207/59 | 14.9 | 0.91 | 0.000 | 0.005 | 0.000 | 0.083 | 0.000 | 0.000 | 0.163 | 0.000 | 0.000 | 0.000 | 0.068 | 0.001 | 0.000 |
| H324/78 | 15.9 | 0.98 | 0.000 | 0.002 | 0.877 | 1.062 | 0.002 | 0.980 | 1.922 | 0.000 | 0.002 | 0.878 | 1.760 | 0.001 | 1.282 |
| H168/79 | 16.8 | 1.03 | 0.000 | 0.636 | 0.129 | 0.841 | 0.284 | 0.178 | 0.026 | 0.000 | 0.145 | 0.125 | 0.026 | 0.148 | 0.232 |
| Sum impurity area[1] % | | | 0.000 | 0.977 | 1.444 | 2.193 | 0.783 | 1.757 | 2.926 | 0.00 | 0.260 | 1.158 | 2.049 | 0.148 | 2.729 |

| Individual impurities | RT/min | RRT | Formulation No. 65 40° C.-3 m | 68 initial | 25° C.-1 m | 40° C.-1 m | 66 initial | 25° C.-1 m | 40° C.-1 m | 64 initial | 25° C.-1 m | 40° C.-1 m |
|---|---|---|---|---|---|---|---|---|---|---|---|---|
| H152/81 | 11.5 | 0.71 | 0.720 | 0.000 | 0.400 | 0.110 | 0.000 | 0.410 | 0.670 | 0.000 | 0.268 | 0.379 |
| S24 or S25 | 13.5 | 0.83 | 0.070 | 0.000 | 0.000 | 0.000 | 0.000 | 0.000 | 0.000 | 0.000 | 0.000 | 0.000 |
| S23 | 13.9 | 0.85 | 0.039 | 0.000 | 0.001 | 0.023 | 0.000 | 0.001 | 0.003 | 0.000 | 0.000 | 0.009 |
| unknown 1 | 14.4 | 0.88 | 0.038 | 0.000 | 0.000 | 0.000 | 0.000 | 0.000 | 0.000 | 0.000 | 0.000 | 0.000 |
| H207/59 | 14.9 | 0.91 | 0.281 | 0.000 | 0.000 | 0.000 | 0.000 | 0.000 | 0.000 | 0.000 | 0.000 | 0.000 |
| H324/78 | 15.9 | 0.98 | 3.177 | 0.000 | 0.000 | 0.002 | 0.000 | 0.000 | 0.000 | 0.000 | 0.000 | 0.000 |
| H168/79 | 16.8 | 1.03 | 0.701 | 0.000 | 0.000 | 0.000 | 0.000 | 0.154 | 0.031 | 0.483 | 0.154 | 0.164 |
| Sum impurity area[1] % | | | 4.879 | 0.00 | 0.400 | 0.110 | 0.00 | 0.564 | 0.670 | 0.483 | 0.422 | 0.543 |

[1]Total impurities is sum of all peaks above Limit of Quantation (0.1%).

Example 14

Evaluation of Oxidative Degradation of Clevidipine

Nanoparticle formulations with clevidipine (formulation numbers 31, 40 and 42) as well as clevidipine solutions were purged either with nitrogen or compressed air, and exposed to ambient light to determine the effect of head space oxygen on the formation of oxidative degradation product, H324/78. The results are summarized in Table 30. The results demonstrated that in general oxidative degradation was reduced when clevidipine was incorporated in the nanoparticle compared to that in solution. Additionally, results showed that it is possible to further reduce formation of oxidative degradant H324/78 by purging with nitrogen.

TABLE 30

Results for Oxidative Degradation of Clevidipine:
Influence of Oxygen Content in Headspace

| Formulation | H324/78 (% Area) |
|---|---|
| 31 N2 | 0.58 |
| 31 Air | 0.65 |
| 40 N2 | 0.84 |
| 40 Air | 1.08 |
| 42 N2 | 0.73 |
| 42 Air | 1.02 |
| Clevidipine N2 | 2.54 |
| Clevidipine Air | 3.06 |

Example 15

Effect of Antioxidant on Oxidative Degradation of Clevidipine

Nanoparticle formulations containing clevidipine were prepared with varying levels of antioxidants (ascorbic acid or sodium ascorbate) and exposed to ambient light for 3 days to determine their effect on the formation of oxidative degradation product H324/78. The antioxidants were added after nanoparticle precipitation and diafiltration and the suspensions were purged with nitrogen or compressed air prior to sealing. Solutions of clevidipine containing an antioxidant were also exposed to ambient light for comparison. A summary of nanoparticle compositions containing clevidipine and antioxidant is provided in Table 31:

TABLE 31

Summary of Aqueous Nanoparticle Compositions containing Antioxidant

| No. | Clevidipine (mg/ml) | Vitamin E (mg/ml) | Deoxycholic acid (mg/ml) | Tween 20 (mg/mL) | Kolliphor EL (mg/mL) | Ascorbic Acid (mg/mL) | Sodium Ascorbate (mg/mL) |
|---|---|---|---|---|---|---|---|
| 69 | 0.42 | 5 | 1.67 | 0.021 | 0 | 0.25 | 0 |
| 70 | 0.42 | 5 | 1.67 | 0.021 | 0 | 0.5 | 0 |
| 71 | 0.42 | 5 | 1.67 | 0.021 | 0 | 0.75 | 0 |
| 72 | 0.23 | 4.55 | 0.91 | 0 | 0.023 | 0.25 | 0 |
| 73 | 0.23 | 4.55 | 0.91 | 0 | 0.023 | 0.5 | 0 |
| 74 | 0.23 | 4.55 | 0.91 | 0 | 0.023 | 0.75 | 0 |
| 75 | 0.42 | 5 | 1.67 | 0.021 | 0 | 0 | 0.1 |
| 76 | 0.42 | 5 | 1.67 | 0.021 | 0 | 0 | 0.25 |
| 77 | 0.42 | 5 | 1.67 | 0.021 | 0 | 0 | 0.5 |
| 78 | 0.42 | 5 | 1.67 | 0.021 | 0 | 0 | 0.75 |
| 79 | 0.42 | 5 | 1.67 | 0.021 | 0 | 0 | 1 |
| STD 1 | 0.2 | 0 | 0 | 0 | 0 | 0 | 0 |
| STD 2 | 0.2 | 0 | 0 | 0 | 0 | 0 | 1 |

Table 32 shows that formation of oxidative degradation product H324/78 was reduced in presence of antioxidant:

TABLE 32

Results for Oxidative Degradation of
Clevidipine: Effect of Antioxidant

| | H324/78 (% Area) | |
|---|---|---|
| No. | Air | Nitrogen |
| 75 | 0.708% | 0.583% |
| 76 | 0.676% | 0.571% |
| 77 | 0.396% | 0.583% |
| 78 | 0.384% | 0.399% |
| 79 | 0.331% | 0.275% |
| STD 1 | 8.968% | 2.400% |
| STD 2 | 1.549% | 0.364% |

The above results show that, by employing adequate controls to minimize oxygen content in the headspace or including an antioxidant or combination of both, it is possible to minimize oxidative degradation of clevidipine in the nanoparticle during long-term storage.

It is to be understood that the invention is not limited to the particular embodiments of the invention described above, as variations of the particular embodiments may be made and still fall within the scope of the appended claims.

The invention claimed is:

1. A method of making a therapeutic nanoparticle, comprising clevidipine, or a pharmaceutically acceptable salt thereof and at least one excipient, said method comprising:
   dissolving clevidipine, or a pharmaceutically acceptable salt thereof, in a first solvent to form a solution,
   pumping the solution comprising clevidipine, or pharmaceutically acceptable salt thereof, through heated capillaries into a heated microjet reactor,
   precipitating the solution with a second solvent using the microjet reactor, and
   removing a portion of the solvents forming a core portion and an outer portion of said nanoparticle;
   wherein the core portion comprises the clevidipine or pharmaceutically acceptable salt thereof, and the outer portion surrounds the core and comprises the at least one excipient,
   wherein the at least one excipient is present in the first solvent and/or the second solvent, wherein the at least one excipient is selected from the group consisting of water insoluble excipients, water soluble excipients and combinations thereof, wherein said water soluble excipient is polyethylene glycol 200 (PEG 200), sodium deoxycholate, vitamin E tocopheryl polyethylene glycol succinate (vitamin E TPGS) or combinations thereof, wherein said water insoluble excipient is vitamin E, deoxycholic acid, phosphotidylcholine or combinations thereof, and storing the nanoparticle for at least three months at room temperature and the level of any single impurity is no more than 1.8% on a weight-to-weight basis.

2. The method according to claim 1, wherein the outer portion comprises at least one water soluble excipient and at least one water insoluble excipient.

3. The method according to claim 1, wherein said using microjet reactor yields the nanoparticles at less than 900 nm in size.

4. The method according to claim 1, wherein said using microjet reactor yields the nanoparticles at less than 800 nm in size.

5. The method according to claim 1, wherein said using microjet reactor yields the nanoparticles at less than 700 nm in size.

6. The method according to claim 1, wherein said using microjet reactor yields the nanoparticles at less than 600 nm in size.

7. The method according to claim 1, wherein said using microjet reactor yields the nanoparticles at less than 500 nm in size.

8. The method according to claim 1, wherein said using microjet reactor yields the nanoparticles at less than 400 nm in size.

9. The method according to claim 1, wherein said using microjet reactor yields the nanoparticles at less than 300 nm in size.

10. The method according to claim 1, wherein said using microjet reactor yields the nanoparticles at less than 200 nm in size.

11. The method according to claim 1, wherein said using microjet reactor yields the nanoparticles at less than 100 nm in size.

12. The method according to claim 1, wherein said using microjet reactor yields the nanoparticles at less than 50 nm in size.

13. The method according to claim 1, wherein said using microjet reactor yields the nanoparticles at from 50 nm to 400 nm in size.

14. The method according to claim 1, wherein said using microjet reactor yields the nanoparticles at from 100 nm to 600 nm in size.

15. The method according to claim 1, wherein said using microjet reactor yields the nanoparticles at from 100 nm to 250 nm in size.

16. The method according to claim 1, wherein said using microjet reactor yields the nanoparticles at from 200 nm to 450 nm in size.

17. The method according to claim 1, wherein the using the microjet reactor comprises
colliding clevidipine, or a pharmaceutically acceptable salt thereof, and said at least one excipient in the microjet reactor.

18. The method according to claim 17, further comprising adding an anti-oxidant.

19. The method according to claim 18, wherein said anti-oxidant is acetylcysteine, ascorbyl palmitate, butylated hydroxyanisole, butylated hydroxytoluene, monothioglycerol, ascorbic acid, sodium ascorbate, sodium formaldehyde sulfoxylate, sodium metabisulfite, sodium bisulfate, propyl gallate, edetate, disodium edetate, diethylenetriaminepentaacetic acid, methionine, histidine, cysteine, arginine, lysine, aspartic acid, glutamic acid, or any combinations thereof.

20. The method according to claim 1 further comprising adding an anti-oxidant.

21. The method according to claim 20, wherein said anti-oxidant is acetylcysteine, ascorbyl palmitate, butylated hydroxyanisole, butylated hydroxytoluene, monothioglycerol, ascorbic acid, sodium ascorbate, sodium formaldehyde sulfoxylate, sodium metabisulfite, sodium bisulfate, propyl gallate, edetate, disodium edetate, diethylenetriaminepentaacetic acid, methionine, histidine, cysteine, arginine, lysine, aspartic acid, glutamic acid, or any combinations thereof.

22. The method according to claim 1, wherein the removing solvents comprises diafiltration or dialysis.

23. A method of making a therapeutic nanoparticle, comprising clevidipine, or a pharmaceutically acceptable salt thereof and at least one excipient, said method comprising:

dissolving clevidipine, or a pharmaceutically acceptable salt thereof, in a first solvent to form a solution, pumping the solution comprising clevidipine, or a pharmaceutically acceptable salt thereof, through heated capillaries into a heated microjet reactor, precipitating the solution with a second solvent using the microjet reactor, and removing a portion of the solvents forming a core portion and an outer portion of said nanoparticle;

wherein the core portion comprises the clevidipine or pharmaceutically acceptable salt thereof, and the outer portion surrounds the core and comprises the at least one excipient, wherein the at least one excipient is present in the first solvent and/or the second solvent, wherein the at least one excipient is selected from the group consisting of water insoluble excipients, water soluble excipients and combinations thereof, wherein said water soluble excipient is polyethylene glycol 200 (PEG 200), sodium deoxycholate, vitamin E tocopheryl polyethylene glycol succinate (vitamin E TPGS) or combinations thereof, and wherein said water insoluble excipient is vitamin E, deoxycholic acid, phosphotidylcholine or combinations thereof, and storing the nanoparticle for at least three months at room temperature and the level of impurities is minimized to no more than 0.2% on a weight-to-weight basis for any of Substance 23, Substance 24, and Substance 25, and no more than 1.5% for H168/79 on a weight-to-weight basis.

24. A method of making a therapeutic nanoparticle comprising clevidipine, or a pharmaceutically acceptable salt thereof, and at least one excipient, said method comprising:

dissolving clevidipine, or a pharmaceutically acceptable salt thereof, in a first solvent to form a solution, pumping the solution comprising clevidipine, or pharmaceutically acceptable salt thereof, through heated capillaries into a heated microjet reactor, precipitating the solution with a second solvent using a microjet reactor, and
removing a portion of the solvents;
wherein clevidipine is stabilized in the nanoparticle with the at least one excipient of the group consisting of water insoluble excipients, and water soluble excipients and combinations thereof,
wherein said water soluble excipient is polyethylene glycol 2000 (PEG 200), sodium deoxycholate, vitamin E tocopheryl polyethylene glycol succinate (vitamin E TPGS) or combinations thereof,
wherein said water insoluble excipient is vitamin E, deoxycholic acid, phosphotidylcholine or combinations thereof,
wherein said clevidipine is a core portion of said nanoparticle, and said at least one excipient comprises an outer portion surrounding said core,
wherein the at least one excipient is present in the first solvent and/or the second solvent, and
storing the nanoparticle for at least three months at room temperature and the level of any single impurity is no more than 1.8% on a weight-to-weight basis.

\* \* \* \* \*